(12) United States Patent
Tsukazaki et al.

(10) Patent No.: US 8,338,133 B2
(45) Date of Patent: Dec. 25, 2012

(54) DNA ENCODING GLYCEROGLYCOLIPID LIPASE

(75) Inventors: Kaoru Tsukazaki, Yokohama (JP); Tetsuya Fukazawa, Yokohama (JP); Isshin Tanaka, Shinagawa (JP)

(73) Assignee: Mitsubishi-Kagaku Foods Corporation, Tokyo (JP)

( * ) Notice: Subject to any disclaimer, the term of this patent is extended or adjusted under 35 U.S.C. 154(b) by 597 days.

(21) Appl. No.: 12/524,742

(22) PCT Filed: Jan. 30, 2008

(86) PCT No.: PCT/JP2008/051386
§ 371 (c)(1),
(2), (4) Date: Jul. 28, 2009

(87) PCT Pub. No.: WO2008/093720
PCT Pub. Date: Aug. 7, 2008

(65) Prior Publication Data
US 2011/0236531 A1    Sep. 29, 2011

(30) Foreign Application Priority Data

Jan. 30, 2007  (JP) ............................. 2007-0187731

(51) Int. Cl.
*C12P 21/06*    (2006.01)
(52) U.S. Cl. ............................. 435/69.1; 435/6; 435/7.1
(58) Field of Classification Search .................. None
See application file for complete search history.

(56) References Cited

U.S. PATENT DOCUMENTS

| | | | |
|---|---|---|---|
| 5,378,623 A | 1/1995 | Hattori et al. | |
| 5,521,080 A | 5/1996 | Hattori et al. | |
| 5,538,874 A | 7/1996 | Hattori et al. | |
| 7,588,925 B2 * | 9/2009 | Albermann et al. | 435/196 |
| 7,666,618 B2 * | 2/2010 | Miasnikov et al. | 435/18 |
| 2002/0064577 A1 | 5/2002 | Soe et al. | |
| 2003/0108641 A1 | 6/2003 | Soe et al. | |
| 2003/0175383 A1 | 9/2003 | Bojsen et al. | |
| 2003/0194467 A1 | 10/2003 | Olsen et al. | |
| 2004/0071853 A1 | 4/2004 | Soe et al. | |
| 2004/0101610 A1 | 5/2004 | Soe et al. | |
| 2005/0281916 A1 | 12/2005 | Bojsen et al. | |
| 2005/0287250 A1 | 12/2005 | Olsen et al. | |
| 2006/0075518 A1 | 4/2006 | Yaver et al. | |
| 2007/0207521 A1 | 9/2007 | Albermann et al. | |
| 2008/0038404 A1 | 2/2008 | Brunstedt et al. | |
| 2010/0047877 A1 | 2/2010 | Albermann et al. | |

FOREIGN PATENT DOCUMENTS

| | | |
|---|---|---|
| JP | 62-171691 | 7/1987 |
| JP | 2005 508609 | 4/2005 |
| JP | 2005 525818 | 9/2005 |
| JP | 3824174 | 7/2006 |
| JP | 2007 528732 | 10/2007 |
| WO | 98 45453 | 10/1998 |
| WO | 02 00852 | 1/2002 |
| WO | 2004 018660 | 3/2004 |
| WO | 2006 008653 | 1/2006 |

OTHER PUBLICATIONS

Zheng et al. (Biotechnol. Letters, vol. 29, pp. 1875-1879, 2007).*
Carr, N. et al., "Lipid Interactions in Breadmaking", Critical Reviews in Food Science and Nutrition, vol. 31, No. 3, pp. 237-258, (1992).
Japanese Office Action issued Dec. 20, 2011, in Patent Application No. 2008-019067 (with English-language translation).

* cited by examiner

*Primary Examiner* — Hope Robinson
(74) *Attorney, Agent, or Firm* — Oblon, Spivak, McClelland, Maier & Neustadt, L.L.P.

(57) ABSTRACT

A glyceroglycolipid lipase which is highly safe, hydrolyzes a neutral fat, a glycerophospholipid or a glyceroglycolipid at about pH 6, is thermally stable, hydrolyzes lecithin, does not hydrolyze lysolecithin, can rise a bread when used singly in the production of the bread, and has no unpleasant odor. Specifically disclosed is a glyceroglycolipid lipase derived from a filamentous bacterium *Aspergillus japonicus*.

15 Claims, 7 Drawing Sheets pH/activity using DGDG as a substrate
Glyceroglycolipid lipase G-2 pH/activity using DGDG as a substrate
Lipopan F purified enzyme pH/activity using lecithin as a substrate
Glyceroglycolipid lipase G-1 pH/activity using lecithin as a substrate
Glyceroglycolipid lipase G-2 pH/stability using DGDG as a substrate
Glyceroglycolipid lipase G-2 pH/stability using DGDG as a substrate
Lipopan F purified enzyme pH/stability using lecithin as a substrate
Glyceroglycolipid lipase G-2

Temperature/activity using DGDG as a substrate
Glyceroglycolipid lipase G-2

Temperature/activity using DGDG as a substrate
Lipopan F purified enzyme

Temperature/activity using lecithin as a substrate
Glyceroglycolipid lipase G-1

Temperature/activity using lecithin as a substrate
Glyceroglycolipid lipase G-2

Temperature/stability using DGDG as a substrate
Glyceroglycolipid lipase G-2

Temperature/stability using DGDG as a substrate
Lipopan F purified enzyme

Temperature/stability using lecithin as a substrate
Glyceroglycolipid lipase G-2

SEQUENCE LISTING

<160> NUMBER OF SEQ ID NOS: 7

<210> SEQ ID NO 1
<211> LENGTH: 1101
<212> TYPE: DNA
<213> ORGANISM: Aspergillus japonicus
<220> FEATURE:
<221> NAME/KEY: CDS
<222> LOCATION: (110)..(991)

<400> SEQUENCE: 1

```
ctagtaacgg ccgccagtgt gctggaattc gcccttgctc cttgcctgtt cgttttggtt      60
atcgacttga cctgggttgg cgctgtatat atactcccaa actgcaagc atg gta tat     118
                                                     Met Val Tyr
                                                       1 ttc act cgt ttg ggt ggg gtg gtg gcc gct ctt gcg gcc ttg gtt gtg       166
Phe Thr Arg Leu Gly Gly Val Val Ala Ala Leu Ala Ala Leu Val Val
        5                  10                  15 gct gct ccg gtt gat att cga gat gtc tcg acc act gtc tac acg cag       214
Ala Ala Pro Val Asp Ile Arg Asp Val Ser Thr Thr Val Tyr Thr Gln
 20                  25                  30                  35 ctg gat ctg ttc gcg caa tac tcc gcc gcg gcg tac tgc tcg acc aac       262
Leu Asp Leu Phe Ala Gln Tyr Ser Ala Ala Ala Tyr Cys Ser Thr Asn
                 40                  45                  50 ctc gat tcc ccg aat acg agc gtg acc tgc acg aac gga ctt tgt ccg       310
Leu Asp Ser Pro Asn Thr Ser Val Thr Cys Thr Asn Gly Leu Cys Pro
             55                  60                  65 tta ctc gca gct gcc acg acc aag agt ctg gcc gag ttc gag gct tct       358
Leu Leu Ala Ala Ala Thr Thr Lys Ser Leu Ala Glu Phe Glu Ala Ser
         70                  75                  80 gat tcc tac ggc gat aca gca gga ttc ctc gtg gtt gac tcc acc aac       406
Asp Ser Tyr Gly Asp Thr Ala Gly Phe Leu Val Val Asp Ser Thr Asn
 85                  90                  95 aag aag ctg gtg gtg tcg ttc cgc gga agc agc tcg att gag aac tgg       454
Lys Lys Leu Val Val Ser Phe Arg Gly Ser Ser Ser Ile Glu Asn Trp
100                 105                 110                 115 atc gcc aat ttg gac ttc atc ttc acg gat gcc agc gcg gtc tgc agt       502
Ile Ala Asn Leu Asp Phe Ile Phe Thr Asp Ala Ser Ala Val Cys Ser
                 120                 125                 130 ggc tgc cag gtc cac cag ggc ttc tgg aag gcc tgg agc tct gtc gcg       550
Gly Cys Gln Val His Gln Gly Phe Trp Lys Ala Trp Ser Ser Val Ala
             135                 140                 145 gac acc ttg acg acg gag atc gcg tct gcg gta acc gct tac ccc ggc       598
Asp Thr Leu Thr Thr Glu Ile Ala Ser Ala Val Thr Ala Tyr Pro Gly
         150                 155                 160 tat agc ctg gtg ttc acg ggg cat agt ctg gga gga gcg ttg gcg acc       646
Tyr Ser Leu Val Phe Thr Gly His Ser Leu Gly Gly Ala Leu Ala Thr
165                 170                 175 atc ggc gcg acg gtg ctg cgg aat gcg gga tac tcc gtt caa ctg tat       694
Ile Gly Ala Thr Val Leu Arg Asn Ala Gly Tyr Ser Val Gln Leu Tyr
180                 185                 190                 195 tcc tat gga gcg ccc cga gtg ggc aac acg gcg ctg gcc aac tat atc       742
Ser Tyr Gly Ala Pro Arg Val Gly Asn Thr Ala Leu Ala Asn Tyr Ile
                 200                 205                 210 acg agc aaa ggc tct ggc tcg aat ttc cga gtg act cac ctc aac gat       790
Thr Ser Lys Gly Ser Gly Ser Asn Phe Arg Val Thr His Leu Asn Asp
             215                 220                 225 gtc gtg cct aga ctt ccg ccg aga ctg ctt ggt tat agt cac cca agc       838
Val Val Pro Arg Leu Pro Pro Arg Leu Leu Gly Tyr Ser His Pro Ser
         230                 235                 240 ccg gaa tac tgg atc act agc gga act ggt gct gca gtg acc tca tcg       886
Pro Glu Tyr Trp Ile Thr Ser Gly Thr Gly Ala Ala Val Thr Ser Ser
245                 250                 255 gat atc gac atc atc cag ggc gtc gac tcc tct gct gga aac gcg ggg       934
Asp Ile Asp Ile Ile Gln Gly Val Asp Ser Ser Ala Gly Asn Ala Gly
260                 265                 270                 275 gag aat atc acc agc gtg ctg gcg cac ctg tgg tac ttc atc agt att       982
Glu Asn Ile Thr Ser Val Leu Ala His Leu Trp Tyr Phe Ile Ser Ile
                 280                 285                 290 ggc act tgt taatcgttgt acatatgtga ggtatgagac aatgtgggaa              1031
Gly Thr Cys
```

```
Gly Thr Cys gggcgaattc tgcagatatc catcacactg gcggccgctc gagcatgcat ctagagggcc    1091
caatcgccct                                                           1101
```

<210> SEQ ID NO 2
<211> LENGTH: 294
<212> TYPE: PRT
<213> ORGANISM: Aspergillus japonicus

<400> SEQUENCE: 2

```
Met Val Tyr Phe Thr Arg Leu Gly Gly Val Ala Ala Leu Ala Ala
1               5                   10                  15

Leu Val Val Ala Ala Pro Val Asp Ile Arg Asp Val Ser Thr Thr Val
                20                  25                  30

Tyr Thr Gln Leu Asp Leu Phe Ala Gln Tyr Ser Ala Ala Tyr Cys
                35                  40                  45

Ser Thr Asn Leu Asp Ser Pro Asn Thr Ser Val Thr Cys Thr Asn Gly
            50                  55                  60

Leu Cys Pro Leu Leu Ala Ala Ala Thr Thr Lys Ser Leu Ala Glu Phe
65                  70                  75                  80

Glu Ala Ser Asp Ser Tyr Gly Asp Thr Ala Gly Phe Leu Val Val Asp
                    85                  90                  95

Ser Thr Asn Lys Lys Leu Val Val Ser Phe Arg Gly Ser Ser Ser Ile
                100                 105                 110

Glu Asn Trp Ile Ala Asn Leu Asp Phe Ile Phe Thr Asp Ala Ser Ala
            115                 120                 125

Val Cys Ser Gly Cys Gln Val His Gln Gly Phe Trp Lys Ala Trp Ser
130                 135                 140

Ser Val Ala Asp Thr Leu Thr Thr Glu Ile Ala Ser Ala Val Thr Ala
145                 150                 155                 160

Tyr Pro Gly Tyr Ser Leu Val Phe Thr Gly His Ser Leu Gly Gly Ala
                165                 170                 175

Leu Ala Thr Ile Gly Ala Thr Val Leu Arg Asn Ala Gly Tyr Ser Val
                180                 185                 190

Gln Leu Tyr Ser Tyr Gly Ala Pro Arg Val Gly Asn Thr Ala Leu Ala
            195                 200                 205

Asn Tyr Ile Thr Ser Lys Gly Ser Gly Ser Asn Phe Arg Val Thr His
            210                 215                 220

Leu Asn Asp Val Val Pro Arg Leu Pro Pro Arg Leu Leu Gly Tyr Ser
225                 230                 235                 240

His Pro Ser Pro Glu Tyr Trp Ile Thr Ser Gly Thr Gly Ala Ala Val
                245                 250                 255

Thr Ser Ser Asp Ile Asp Ile Ile Gln Gly Val Asp Ser Ser Ala Gly
            260                 265                 270

Asn Ala Gly Glu Asn Ile Thr Ser Val Leu Ala His Leu Trp Tyr Phe
            275                 280                 285

Ile Ser Ile Gly Thr Cys
    290
```

<210> SEQ ID NO 3
<211> LENGTH: 19
<212> TYPE: PRT
<213> ORGANISM: Aspergillus japonicus
<220> FEATURE:
<223> OTHER INFORMATION: Partial sequence from N-terminus of glyceroglycolipid of strain SANK 11298.

```
<400> SEQUENCE: 3

Asp Val Ser Thr Thr Val Tyr Thr Gln Leu Asp Leu Phe Ala Gln Tyr
1               5                   10                  15

Ser Ala Ala

<210> SEQ ID NO 4
<211> LENGTH: 23
<212> TYPE: DNA
<213> ORGANISM: Artificial
<220> FEATURE:
<223> OTHER INFORMATION: primer

<400> SEQUENCE: 4
gcacacttca tgcatcatat aca                                      23

<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5
cccacattgt ctcatacctc a                                        21

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
cgtctgcgtt tgctgatatt                                          20

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
gctccttgcc tgttcgtttt                                          20
```

DNA ENCODING GLYCEROGLYCOLIPID LIPASE

TECHNICAL FIELD

The present invention relates to a glyceroglycolipid lipase, a filamentous fungus producing the lipase, a method for separating and purifying the lipase from a cultured product of a filamentous fungus, DNA encoding the lipase, a method for producing the lipase, and the like. Specifically, the present invention relates to the lipase which is particularly suitable for use in the food industry and the pharmaceutical industry, particularly a glyceroglycolipid lipase derived from a filamentous fungus *Aspergillus japonicus*, a filamentous fungus producing the lipase, a method for separating and purifying the lipase from a cultured product of a filamentous fungus, DNA encoding the lipase, a method for producing the lipase, a method for baking using the lipase, and the like.

BACKGROUND ART

[1] Glycolipid Lipase

It is known that plants and microorganisms produce lipases that hydrolyze glyceroglycolipids. Enzymes derived from plants have the ability to hydrolyze mainly glycerophospholipids and glyceroglycolipids, although the ability to hydrolyze neutral fats, particularly triglycerides, is extremely low. Among microorganisms, lipases derived from *actinomyces*, bacteria, and molds are known. Lipases derived from *actinomyces* and bacteria have the property of hydrolyzing also glycerophospholipids in addition to glyceroglycolipids. It is known that lipases derived from filamentous fungi hydrolyze neutral fats, glycerophospholipids and glyceroglycolipids. As used herein, "a glyceroglycolipid lipase" refers to an enzyme that has an activity of hydrolyzing glyceroglycolipid into lysoglyceroglycolipid and fatty acid (hereinafter referred to as "glyceroglycolipid degradation activity"). A digalactosyldiacylglycerol degradation activity (hereinafter referred to as "DGDG degradation activity") is a concept included in the glyceroglycolipid degradation activity. According to the present invention, "relative degradation activity" is defined to be a relative value of a DGDG degradation activity or a lecithin degradation activity under given pH or temperature conditions defining, as 100%, the DGDG degradation activity or the lecithin degradation activity under specific pH or temperature conditions that result in the highest activity. In addition, according to the present invention, "relative residual degradation activity" is defined to be a relative value of a DGDG degradation activity or a lecithin degradation activity under given pH or temperature conditions after treatment under the given pH or temperature conditions defining, as 100%, the DGDG degradation activity or the lecithin degradation activity under specific pH or temperature conditions that result in the highest activity after treatment under the specific pH or temperature conditions.

As to lipases derived from bacteria that hydrolyze glyceroglycolipids, for example, lipases derived from *Cornebacterium efficiens, Thermobifida fusca*, and the like are known (Patent Document 1).

As to lipases derived from *actinomyces* that hydrolyze glyceroglycolipids, for example, lipases derived from *Streptomyces* sp. are known (Patent Document 1).

As to lipases derived from molds that hydrolyze glyceroglycolipids, for example, lipases derived from *Fusarium venenatum, Fusarium sulfureum, Fusarium culmorum, Fusarium solani, Fusarium oxysporum, Acremonium berkeleyanum, Aspergillus fumigatus, Aspergillus nidulans, Aspergillus niger*, and the like are known (Patent Documents 2-4).

[2] Glycerolipid

Glyceroglycolipids are distributed mainly among Gram-positive bacteria and chloroplasts of higher plants. Glyceroglycolipid is a compound having a sugar chain covalently bonding to the 3-position of 1,2-diacylglycerol. Galactose or the like is included as the sugar chain, and the composition ratios differ depending on the sources. For example, monogalactosyldiacylglycerol (hereinafter referred to as "MGDG"), digalactosyldiacylglycerol (hereinafter referred to as "DGDG") and the like are included in glyceroglycolipids.

Glycerophospholipids are widely distributed among animals, plants and fungi. Glycerophospholipid is a compound having a phosphoryl base covalently bonding to the 3-position of 1,2-diacylglycerol. Choline, ethanolamine, serine, inositol, glycerol or the like is included as the base, and the composition ratios differ depending on the sources. For example, lecithin and the like are include in glycerophospholipids.

Neutral fats are also widely distributed among animals, plants and fungi. Neutral fat is a generic term for monoacylglycerol, diacylglycerol and triacylglycerol.

[3] Enzymatic Treatment of Lecithin or Glyceroglycolipid

Lecithin or glyceroglycolipid has two hydrophobic fatty acid moieties in the molecule, and is known as a lipophilic surfactant. Hydrolysis of one of them with a lipase increases the hydrophilicity, resulting in a substance having properties different from those of the lecithin or the glyceroglycolipid. Actually, since lysolecithin generated as a result of action by a phospholipase on lecithin is water soluble, and the physical properties of a food obtained using the lysolecithin as a food additive differ from those of the lecithin, its application in the food industry is examined.

Also in case of glyceroglycolipid, it is possible to produce lysoglyceroglycolipid by partially hydrolyzing it with a glyceroglycolipid lipase. Lysoglyceroglycolipid is also a substance with increased hydrophilicity. For example, lysoglyceroglycolipids include digalactosylmonoglyceride (hereinafter referred to as "DGMG") and the like.

[4] Use of Glyceroglycolipid Lipase in Food

By using a glyceroglycolipid lipase, it is possible to produce lysoglyceroglycolipid from glyceroglycolipid in the presence of water as shown below:

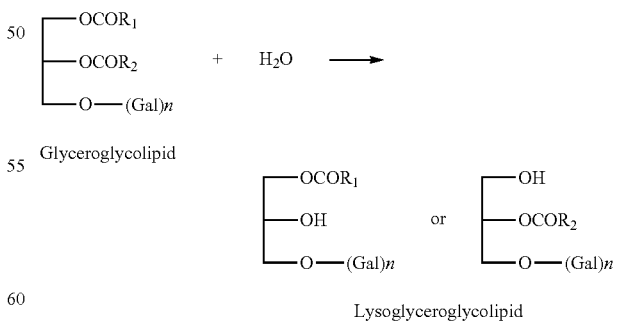

wherein each of $R_1$ and $R_2$ represents an alkyl group, and Gal represents galactose.

If the enzyme also has a lecithin degradation activity, it is possible to simultaneously produce lysolecithin, which is lysoglycerophospholipid, from lecithin:

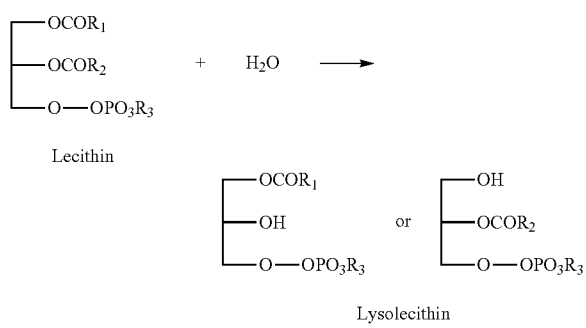

Lecithin

Lysolecithin wherein each of $R_1$ and $R_2$ represents an alkyl group, and $R_3$ represents a base such as choline, ethanolamine, glycerol, inositol or the like.

It is possible to provide a product containing a hydrophilic surfactant by leading such a reaction in a food material.

In addition, since various processes are performed on food in the range of neutral to weak acid in many cases in the food industry in order to prevent deterioration of foods, it is desirable that an enzyme preparation has a high activity in this pH range.

[5] Use of Glyceroglycolipid Lipase for Baking

Upon baking, a chemically synthesized surfactant is used in many cases for increasing the volume, improving the texture, or the like. However, baking without adding a synthetic surfactant is desirable since nature-oriented trend is growing recently. In addition, oils and fats, egg yolks, and the like are added to bread for improving the texture. However, baking without adding such an additive is also desirable since health-oriented trend is growing or the issue of allergy is serious.

It is known that flours used for baking contain neutral fats, glyceroglycolipids, glycerophospholipids, and the like (Non-patent Document 1). Among these, glyceroglycolipids and glycerophospholipids are expected to serve as surfactants, although their performance is disappointing because of their lipophilicity. Then, it would be possible to sufficiently bring out the performance by partially hydrolyzing these lipids into lysoglyceroglycolipids and lysoglycerophospholipids, which are hydrophilic surfactants. If surfactants could be supplied by components of flour itself, the use of synthetic surfactants would be unnecessary or the amount to be used could be reduced. It is known that, among flour components, the content of glyceroglycolipids is more than that of glycerophospholipids (Non-patent Document 1). Thus, it is desired in the field of baking to produce lysoglyceroglycolipids by hydrolyzing glyceroglycolipids more efficiently as compared with glycerophospholipids to increase the surface-active ability. Furthermore, it is desirable that the enzymatic activities on the produced lysoglyceroglycolipids and lysolecithins are low. In other words, it is desirable that the enzymatic activity on lysophosphatidylcholines (hereinafter referred to as "LPCs") is low.

It has been shown that an enzyme that also hydrolyzes neutral fat in addition to glyceroglycolipid and glycerophospholipid is effective for baking (Patent Document 5). On the other hand, there is also an instance where an enzyme that hardly hydrolyzes neutral fat is more effective for baking (Patent Document 6).

Furthermore, in baking, raw materials are mixed at around pH 6 and incubated at 30-42° C. for fermentation in many cases. Thus, it is desirable that the glyceroglycolipid lipase to be used has an activity and is stable under these conditions.

[6] Problems of Known Glyceroglycolipid Lipases

Lipases derived from plants have problems with their universal use. There has been no detailed description on lipases derived from bacteria. Glyceroglycolipid lipases derived from *actinomyces* additionally have a lecithin degradation activity. Furthermore, many of lipases derived from filamentous fungi are derived from pathogens, thus causing some problems concerning the safety. Furthermore, the properties of the enzymes have not been described in detail. For example, it is presumed that a lipase derived from *Fusarium oxysporum*, which is a plant pathogen, is effective also for actual baking. However, the optimum pH of the lipase is around 9, whereas the enzymatic activity at pH 6, which is essential for baking, is only 35% or less of the enzymatic activity at the optimum pH. Regarding a lipases derived from a non-pathogen *Aspergillus niger*, although the enzymatic activity at pH 4.5 or 5 has been described, the activity at around pH 6, which is considered to be essential for baking, has not been shown and the effectiveness thereof is unknown.

As described above, the heretofore known glyceroglycolipid lipases have problems that: it is highly possible that they only bring insufficient effects; they have problems concerning the safety; the enzymatic reactions are inefficient; or the like. Desirable properties of glyceroglycolipid lipases include being derived from a microorganism without a problem concerning safety, having the ability to efficiently hydrolyze glyceroglycolipid and glycerophospholipid at around pH 6, being thermostable to some extent, and not hydrolyzing lysolecithin.

[Patent Document 1] WO 2006008653
[Patent Document 2] WO 2002000852
[Patent Document 3] US 2006075518
[Patent Document 4] WO 2004018660
[Patent Document 5] Japanese Patent No. 3824174
[Patent Document 6] Japanese Laid-Open Patent [Kohyo] Publication No. 2007-528732
[Non-patent Document 1] Carr N. et. al., Critical Reviews in Food Science and Nutrition, 1992, Vol. 31, p. 237-258

DISCLOSURE OF INVENTION

Problems to be Solved by the Invention

As described above, desirable properties of glyceroglycolipid lipases include being derived from a microorganism without a problem concerning safety, having the ability to efficiently hydrolyze glyceroglycolipid at around pH 6, and being thermostable to some extent. In addition, glyceroglycolipid lipases desirably have properties of hydrolyzing lecithin and not hydrolyzing lysolecithin.

In addition, in the field of baking, conventional lipases have had defects that the swelling effect is little when used alone, and there remains an unsuitable smell for food such as a cheese-like smell. Thus, development of a glyceroglycolipid lipase that has a swelling effect when used alone, and does not result in an unsuitable residual smell has been desired.

Providing such a glyceroglycolipid lipase has been of great interest in this technical field.

Means of Solving the Problems

As a result of intensive studies to find a glyceroglycolipid lipase which has properties of being excellently safe, having the ability to efficiently hydrolyze glyceroglycolipid at around pH 6, being thermostable to some extent, hydrolyzing lecithin, and not hydrolyzing lysolecithin, which, when used for baking, has a swelling effect when used alone, does not result in a residual unsuitable residual smell, and efficiently hydrolyzes glyceroglycolipid which is contained in flour in a larger quantity than glycerophospholipid, the present inventors purified a glyceroglycolipid lipase derived from *Aspergillus japonicus* strain SANK 11298 and cloned the gene for the same, thereby completing the present invention.

Specifically, the present invention relates to:

(1) A glyceroglycolipid lipase having the following properties:
1) having a molecular weight of approximately 29,000 as determined by SDS-PAGE;
2) hydrolyzing neutral fat, lecithin, and glyceroglycolipid at pH 6.0;
3) having a glyceroglycolipid degradation activity at least 10-fold higher than a lecithin degradation activity at pH ranging from 3.6 to 8.9, (2) The glyceroglycolipid lipase according to (1), which further has the following properties:
4) having a relative degradation activity of at least 80% or more for glyceroglycolipid at pH ranging from 4.1 to 7.7;
5) having a relative degradation activity of at least 80% or more for lecithin at pH ranging from 5.1 to 7.1;
6) not having the hydrolytic activity of 5) at a temperature of 80° C. or higher;
7) having a relative residual degradation activity of 75% or more for glyceroglycolipid at pH ranging from 4.1 to 10.7, (3) The glyceroglycolipid lipase according to (1) or (2), which is derived from a filamentous fungus *Aspergillus japonicus*, (4) The glyceroglycolipid lipase according to (3), wherein the filamentous fungus is *Aspergillus japonicus* strain SANK 11298, (5) A glyceroglycolipid lipase which is a protein of any one of the following a) to e):
a) a protein consisting of the amino acid sequence of SEQ ID NO: 2 of the sequence listing;
b) a protein consisting of an amino acid sequence encoded by the nucleotide sequence from nucleotide number 110 to nucleotide number 991 of SEQ ID NO: 1 of the sequence listing;
c) a protein consisting of an amino acid sequence in which one or several amino acids are substituted, deleted, inserted, or added in the amino acid sequence as recited in a) or b), and having a glyceroglycolipid degradation activity;
d) a protein consisting of an amino acid sequence having an amino acid sequence homology of 70% or more with the protein of a), and having a glyceroglycolipid degradation activity;
e) a protein comprising the amino acid sequence as recited in a) or b), (6) DNA described in any one of the following a) to e):
a) DNA consisting of the nucleotide sequence from nucleotide number 110 to nucleotide number 991 of SEQ ID NO: 1 of the sequence listing;
b) DNA consisting of a nucleotide sequence having a nucleotide sequence homology of 70% or more with the DNA of a), and encoding a protein having a glyceroglycolipid degradation activity;
c) DNA hybridizing to the DNA of a) under stringent conditions, and encoding a protein having a glyceroglycolipid degradation activity;
d) DNA encoding a protein consisting of the amino acid sequence of SEQ ID NO: 2 of the sequence listing;
e) DNA comprising the nucleotide sequence from nucleotide number 110 to nucleotide number 991 of SEQ ID NO: 1 of the sequence listing.

(7) A glyceroglycolipid lipase encoded by the DNA according to (6), (8) An isolated filamentous fungus *Aspergillus japonicus* strain SANK 11298, which has the ability to produce the glyceroglycolipid lipase according to any one of (1) to (5) and (7).

(9) A method for producing a glyceroglycolipid lipase, comprising 1) and 2):
1) a step of culturing *Aspergillus japonicus* under conditions under which a glyceroglycolipid lipase is produced, and
2) a step of separating and purifying the glyceroglycolipid lipase from the culture product of 1),

(10) The method according to (9), wherein said *Aspergillus japonicus* is *Aspergillus japonicus* strain SANK 11298,

(11) A glyceroglycolipid lipase which is produced by the method according to (9) or (10),

(12) A method for baking, wherein the glyceroglycolipid lipase according to any one of (1) to (5), (7) and (11) is used,

(13) The glyceroglycolipid lipase according to any one of (1) to (5), (7) and (11), which is for baking.

BEST MODE FOR CARRYING OUT THE INVENTION

Figure 1:
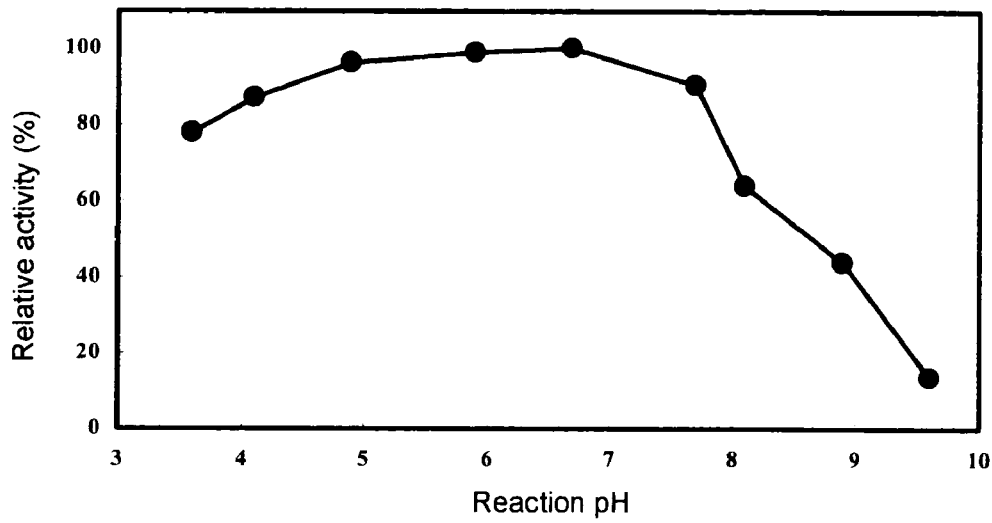
FIG. 1: pH/activity of the purified glyceroglycolipid lipase G-2 derived from strain SANK 11298 using DGDG as a substrate.

Hereinafter, the present invention will be explained in detail.

The present invention relates to a glyceroglycolipid lipase derived from *Aspergillus japonicus*, which is a filamentous fungus useful for degrading glyceroglycolipid.

The glyceroglycolipid lipases of the present invention include a protein having an activity of degrading glyceroglycolipid in a culture of a microorganism producing a glyceroglycolipid lipase. Examples of such glyceroglycolipid lipases include a glyceroglycolipid lipase derived from *Aspergillus japonicus*. A glyceroglycolipid lipase derived from *Aspergillus japonicus* strain SANK 11298 is more preferable.

Another example of the glyceroglycolipid lipases of the present invention is a protein consisting of the amino acid sequence of SEQ ID NO: 2 of the sequence listing.

A protein consisting of the amino acid sequence of SEQ ID NO: 2 of the sequence listing in which one or several amino acid residues are substituted, deleted, inserted, and/or added at one or several sites is also included in the present invention as long as it has a glyceroglycolipid degradation activity. Several means a number that does not exceed 10, preferably a number that does not exceed 5. As to an example of proteins having a substituted amino acid sequence and having an activity equivalent to that of a naturally-occurring protein, for example, it is known that a protein obtained by converting a nucleotide sequence corresponding to cysteine into a nucleotide sequence corresponding to serine in an interleukin 2 (IL-2) gene retains an IL-2 activity (Wang, A. et al. (1984) Science 224, 1431-1433).

As an example of the proteins of the present invention, a protein having a nucleotide sequence homology of 70% or more, more preferably 80% or more, even more preferably 90% or more, particularly preferably 95% or more with a protein consisting of the amino acid sequence of SEQ ID NO: 2 of the sequence listing is also included in the present invention as long as it has a glyceroglycolipid degradation activity.

According to the present invention, "the DNA of the present invention" refers to DNA encoding the glyceroglycolipid lipase of the present invention. The DNA may assume any form known up to now such as cDNA, genomic DNA, artificially modified DNA, or chemically synthesized DNA.

Examples of the DNA of the present invention include DNA of the nucleotide sequence from nucleotide number 110 to nucleotide number 991 of SEQ ID NO: 2 of the sequence listing that encodes a protein having a glyceroglycolipid degradation activity.

Another example of the DNA of the present invention is DNA having a nucleotide sequence homology of 70% or more, more preferably 80% or more, even more preferably 90% or more, particularly preferably 95% or more with the nucleotide sequence from nucleotide number 110 to nucleotide number 991 of SEQ ID NO: 2 of the sequence listing and encoding a protein having a glyceroglycolipid degradation activity. Such DNA includes a mutant DNA found in nature, an artificially modified mutant DNA, and a homologous DNA derived from an organism of different species.

Another example of the DNA of the present invention is DNA hybridizing to the nucleotide sequence from nucleotide number 110 to nucleotide number 991 of SEQ ID NO: 2 of the sequence listing under stringent conditions and encoding a protein having a glyceroglycolipid degradation activity.

The "stringent conditions" according to the present invention include, for example, the conditions as described in Sambrook et al. (eds.) "Molecular Cloning: A Laboratory Manual 2nd Ed., Cold Spring Harbor Laboratory Press (1989), or the like. Specifically, exemplary conditions include the steps of: (i) incubating with a probe at 42° C. overnight in a solution containing 6×SSC (composition of 1×SSC: 0.15M NaCl, 0.015M sodium citrate, pH 7.0), 0.5% SDS, 5×Denhardt's, 100 μg/mL denatured fragmented salmon sperm DNA and 50% formamide; (ii) removing the nonspecifically hybridized probe by washing, wherein, in view of increased accuracy, the washing may be conducted under conditions of lower ionic strength, for example in 2×SSC, more stringently in 0.1×SSC, and/or under conditions of higher temperature, for example at a temperature 40° C. or less lower, more stringently 30° C. or less lower, even more stringently 25° C. or less lower, still more stringently 10° C. or less lower than the Tm value for the nucleic acid to be used; specifically, at 25° C. or higher, more stringently 37° C. or higher, even more stringently 42° C. or higher, still more stringently 50° C. or higher, yet still more stringently 60° C. or higher, etc. although the conditions vary depending on the Tm value of the nucleic acid to be used.

Tm can be determined, for example, according to the following equation: $Tm=81.5+16.6(\log [Na+])+0.41(\% G+C)-(600/N)$, wherein N is the chain length of the oligonucleotide, and % G G+C is the content of guanine and cytosine residues in the oligonucleotide.

Another example of the nucleotides of the present invention is DNA encoding a protein consisting of the amino acid sequence of SEQ ID NO: 2 of the sequence listing. A codon corresponding to an amino acid of interest may arbitrarily be selected. It can be determined according to a conventional method, for example, taking the codon usage of the host to be utilized into consideration (Grantham, R. et al. (1981) Nucleic Acids Res. 9, 143-174). Furthermore, codons of a nucleotide sequence can be partially modified according to a conventional method, such as the site-directed mutagenesis method utilizing primers consisting of synthetic oligonucleotides encoding the desired modification(s) (Mark, D. F. et al. (1984) Proc. Natl. Acad. Sci. USA 81, 5662-5666).

Another example of the DNA of the present invention is DNA consisting of the nucleotide sequence from nucleotide number 110 to nucleotide number 991 of SEQ ID NO: 2 of the sequence listing. In addition, DNA that comprises DNA consisting of the nucleotide sequence from nucleotide number 110 to nucleotide number 991 of SEQ ID NO: 2 of the sequence listing is also included in the present invention as long as it contains a region encoding a protein having a glyceroglycolipid degradation activity.

Furthermore, the glyceroglycolipid lipases of the present invention include a protein consisting of an amino acid sequence encoded by the DNA of the present invention. A mutant in which one or two or more arbitrary amino acid(s) is(are) deleted in the glyceroglycolipid lipase of the present invention can be produced according to a method in which DNA is deleted from the terminus using an exonuclease Bal31, or the like (Toshimitsu Kishimoto et al., "Zoku-Seika-gaku Jikken Koza 1, Idenshi Kenkyuho II (Sequel to Biochemical Experiment Lecture 1, Genetic Research Method II)" 335-354), a cassette mutagenesis method (Toshimitsu Kishimoto, "Shin-Seikagaku Jikken Koza 2, Kakusan III Kumikae DNA Gijutsu (New Biochemical Experiment Lecture 2, Nucleic Acid III—Recombinant DNA Technique)" 242-251), or the like. Thus, even a protein obtained using genetic engineering techniques on the basis of the DNA of the present invention is included in the present invention as long as it has a glyceroglycolipid degradation activity. Such a glyceroglycolipid lipase does not necessarily need to have the whole amino acid sequence of SEQ ID NO: 2 of the sequence listing. For example, even a protein consisting of a partial sequence thereof is included in the glyceroglycolipid lipases of the present invention as long as the protein has a glyceroglycolipid degradation activity. In addition, DNA encoding such a glyceroglycolipid lipase is also included in the present invention.

The glyceroglycolipid lipase used in the present invention may be one purified or partially purified from a culture of a glyceroglycolipid lipase-producing microorganism, a homogenate of cells, or a cell culture supernatant used as it is. It is preferable to culture a glyceroglycolipid lipase-producing microorganism in a medium with the addition of a surfactant in addition to carbon sources and nitrogen sources. Alternatively, it is preferable to culture the microorganism in a medium made from natural materials such as soybean powder, ground sesame, cottonseed meal, or rice bran. The surfactants include TRITON®, TWEEN® sucrose fatty acid ester, sodium cholate, sodium deoxycholate, saponin, and the like.

A glyceroglycolipid lipase-producing microorganism can be cultured using a conventional culture apparatus and a conventional medium. A method of liquid culture, solid culture or the like can be suitably selected for culture. In case of liquid culture, the culture can be carried out in a flask or using a fermenter. A batch culture method without adding further culture medium after the initiation of culture or a fed-batch culture method with adding culture medium as needed during culture can be employed. Carbon and nitrogen sources are added to the medium, and vitamins, trace metal elements, or the like can be added as needed. The carbon sources include monosaccharides such as glucose, mannose, galactose and fructose, disaccharides such as maltose, cellobiose, isomaltose, lactose and sucrose, polysaccharides such as starch, and malt extract, although the carbon source is not limited to the above as long as the glyceroglycolipid lipase-producing microorganism grows therewith. Inorganic nitrogens such as ammonia, ammonium sulfate or ammonium nitrate, or organic nitrogens such as yeast extract, malt extract, corn steep liquor or peptone are used as nitrogen sources, although the nitrogen sources are not limited to the above as long as the glyceroglycolipid lipase-producing microorganism grows therewith. Furthermore, surfactants such as TRITON®, TWEEN® sucrose fatty acid ester, sodium cholate, sodium deoxycholate, lecithin or saponin can be added to the medium in order to increase the yield of a glyceroglycolipid lipase from a glyceroglycolipid lipase-producing microorganism. The amounts of compositions in such a medium can suitably be selected. Culture temperature, pH, and amount of aeration/agitation can suitably be selected so that they are suitable for the production of glyceroglycolipid lipase.

A culture supernatant, which is obtained by removing cells after completing the culture of a glyceroglycolipid lipase-producing microorganism, can be used as it is as a crude enzyme solution. Alternatively, one obtained by purifying or partially purifying the crude enzyme solution by conventional reconstitution treatment, treatment with a protein precipitating agent (salt precipitation method), centrifugation, osmotic shock method, freeze-thaw method, sonication, ultrafiltration, gel filtration, various liquid chromatographies such as adsorption chromatography, ion exchange chromatography, affinity chromatography or high performance liquid chromatography (HPLC), dialysis method, or a combination thereof can also be employed.

As is well known, a filamentous fungus may be readily mutated in nature or by an artificial procedure (e.g., ultraviolet irradiation, radiation, treatment with a chemical agent). The same is true for *Aspergillus japonicus* according to the present invention. *Aspergillus japonicus* according to the present invention includes all the mutants thereof. The mutants also include those obtained by a genetic method such as recombination, transduction or transformation. That is, all of *Aspergillus japonicus* producing a glyceroglycolipid lipase, mutants thereof, and strains that are not clearly distinguished therefrom are included in *Aspergillus japonicus*.

Also, the glyceroglycolipid lipase of the present invention can be obtained from a culture product of a host cell transformed with a recombinant plasmid having the DNA of the present invention inserted in a vector. A recombinant plasmid having the DNA of the present invention inserted in a suitable vector as described above is also included in the present invention. Various commonly known vectors can be used as a vector to be used for such a purpose. Preferable vectors include, but are not limited to, vectors for prokaryotic cells, vectors for eukaryotic cells and vectors for mammal-derived cells. A host cell from other prokaryotes or other eukaryotes can be transformed with such a recombinant plasmid. Furthermore, it is possible to express a gene in each host by using a vector having a suitable promoter sequence and/or a sequence related to phenotypic expression, or by introducing such a sequence to prepare an expression vector. Such an expression vector is a preferable aspect of the recombinant plasmid according to the present invention.

A host cell can be obtained by introducing the recombinant plasmid according to the present invention into one of various cells. The cell may be a prokaryotic cell or a eukaryotic cell as long as a plasmid can be introduced into the cell.

Prokaryotic host cells include, for example, *Escherichia coli* and *Bacillus subtilis*. For transforming such a host cell with a gene of interest into, the host cell is transformed with a plasmid vector containing a regulatory sequence and a replicon, i.e., an origin of replication, derived from a species compatible with the host. A vector having a sequence that can confer selectivity by a phenotypic character (phenotype) to the transformed cell is preferable as a vector.

For example, strain K12, or the like is often used as *Escherichia coli*, and pBR322 or a pUC-series plasmid is generally used as a vector, although they are not limited to the above, and any one of various known strains and vectors can also be used.

Promoters for *Escherichia coli* include tryptophan (trp) promoter, lactose (lac) promoter, tryptophan-lactose (tac) promoter, lipoprotein (lpp) promoter, and polypeptide chain elongation factor Tu (tufB) promoter. Any one of the promoters can be used for the production of the glyceroglycolipid lipase of the present invention.

For example, strain 207-25 is preferable as *Bacillus subtilis*, and pTUB228 (Ohmura, K. et al. (1984) J. Biochem. 95, 87-93) or the like is used as a vector, although they are not limited to the above.

Extracellular secretory expression is also enabled by linking, as a promoter, a DNA sequence encoding a signal peptide sequence of α-amylase from *Bacillus subtilis*.

Eukaryotic host cells include those from vertebrates, insects, yeasts, and the like. As a vertebrate cell, a cell derived from a mammal such as COS cell which is a monkey cell (Gluzman, Y. (1981) Cell 23, 175-182, ATCC CRL-1650), a dihydrofolate reductase-deficient strain (Urlaub, G. and Chasin, L. A. (1980) Proc. Natl. Acad. Sci. USA 77, 4126-4220) of Chinese hamster ovary cell (CHO cell, ATCC CCL-61) or the like is often used, although it is not limited to the above.

A promoter normally located upstream of a gene to be expressed, one having an RNA splice site, a polyadenylation site, a transcription termination sequence, or the like can be used as an expression promoter for a vertebrate cell. It may further have an origin of replication as needed. Examples of the expression vectors include, but are not limited to, pSV2dhfr which has an SV40 early promoter (Subramani, S. et al. (1981) Mol. Cell. Biol. 1, 854-864).

In exemplary case where COS cell is used as a host cell, an expression vector that has the SV40 origin of replication, is capable of autonomously replicating in COS cell, and further is equipped with a transcription promoter, a transcription termination signal, and an RNA splice site can be used as an expression vector. The expression vector can be incorporated into COS cell by the diethylaminoethyl (DEAE)-dextran method (Luthman, H. and Magnusson, G. (1983) Nucleic Acids Res, 11, 1295-1308), the calcium phosphate-DNA co-precipitation method (Graham, F. L. and van der Eb, A. J. (1973) Virology 52, 456-457), the electric pulse perforation method (Neumann, E. et al. (1982) EMBO J. 1, 841-845) or the like, and thus a desired transformed cell can be obtained. When CHO cell is used as a host cell, a transformed cell that stably produces the glyceroglycolipid lipase of the present invention can be obtained by co-transfecting a vector capable of expressing a neo gene which functions as an antibiotic G418 resistance marker such as pRSVneo (Sambrook, J. et al. (1989): "Molecular Cloning A Laboratory Manual" Cold Spring Harbor Laboratory, NY), pSV2-neo (Southern, P. J. and Berg, P. (1982) J. Mol. Appl. Genet. 1, 327-341) or the like along with an expression vector, and selecting G418 resistant colonies.

When an insect cell is used as a host cell, an established cell line (Sf-9 or Sf-21) derived from an ovarian cell of *Spodoptera frugiperda* belonging to the family Noctuidae, the order Lepidoptera, High Five cell derived from an ovum of *Trichoplusia ni* (Wickham, T. J. et al, (1992) Biotechnol. Prog. I: 391-396), or the like is often used as a host cell. pVL1392/1393 which utilizes a promoter for polyhedrin protein of *Autographa* nuclear polyhedrosis virus (AcNPV) is often used as a baculovirus transfer vector (Kidd, I. M. and V. C. Emery (1993) The use of baculoviruses as expression vectors. Applied Biochemistry and Biotechnology 42, 137-159). In addition, a vector that utilizes a promoter for P10 or basic protein of baculovirus can also be used. Furthermore, it is also possible to express a recombinant protein as a secretory protein by linking a secretion signal sequence of an AcNPV envelope surface protein GP67 to the N terminus of the protein of interest (Zhe-mei Wang, et al. (1998) Biol. Chem., 379, 167-174).

Yeasts are generally well known as expression systems for eukaryotic microorganisms as host cells. Among these, yeasts of the genus *Saccharomyces* such as a baker's yeast *Saccharomyces cerevisiae*, and a petroleum yeast *Pichia pastoris* are preferable. For example, a promoter for alcohol dehydrogenase gene (Bennetzen, J. L. and Hall, B. D. (1982) J. Biol. Chem. 257, 3018-3025), a promoter for acid phosphatase gene (Miyanohara, A. et al. (1983) Proc. Natl. Acad. Sci. USA 80, 1-5), or the like can preferably be utilized as an expression vector for a eukaryotic microorganism such as yeast. For expression as a secretory protein, it can be expressed as a recombinant having, at the N terminus, a secretion signal sequence and a cleavage site for an endogenous protease contained in a host cell or a known protease. For example, it is known that, in a system in which human mast cell tryptase, a trypsin-type serine protease, is expressed in a petroleum yeast, active tryptase is secreted into a medium by linking, at the N terminus, a secretion signal sequence of yeast α-factor and a cleavage site for KEX2 protease contained in the petroleum yeast, and expressing it (Andrew, L. Niles, et al. (1998) Biotechnol. Appl. Biochem. 28, 125-131).

The transformant obtained as described above can be cultured according to a conventional method, and the glycero-glycolipid lipase of the present invention is produced as a result of the culture intracellularly or extracellularly. One of conventionally used various media can be selected suitably as a medium used for the culture depending on the host cell employed. For example, in case of the above-mentioned COS cell, a medium such as RPMI1640 medium or Dulbecco's modified Eagle's medium (hereinafter referred to as "DMEM") to which serum components (e.g., fetal calf serum) are added as needed can be used. As to culture conditions, $CO_2$ concentration may range from 0 to 50%, and the concentration is preferably 1 to 10%, more preferably 5%. Culture temperature may range from 0 to 99° C., and the temperature is preferably 20 to 50° C., more preferably 35 to 40° C.

The glyceroglycolipid lipase of the present invention produced as a recombinant protein inside or outside the transformed cell as a result of the above-mentioned culture can be separated and purified from the culture product by various separation procedures utilizing the physicochemical properties, the chemical properties, the biochemical properties (e.g., enzymatic activity) or the like of the protein (see "Seikagaku Data Book II (Biochemistry Data Book II)," p 1175-1259, 1st edition 1st printing, Jun. 23, 1980, Tokyo Kagaku Dojin; Biochemistry, vol. 25, No. 25, p 8274-8277 (1986); Eur. J. Biochem., 163, p 313-321 (1987), etc.). Specifically, the methods are exemplified by conventional reconstitution treatment, treatment with a protein precipitating agent (salt precipitation method), centrifugation, osmotic shock method, freeze-thaw method, sonication, ultrafiltration, gel filtration, various liquid chromatographies such as adsorption chromatography, ion exchange chromatography, affinity chromatography, and high performance liquid chromatography (HPLC), dialysis method, or a combination thereof. A recombinant protein of interest can be produced on an industrial scale with high yield as a result of the above-mentioned procedures. Linking of 6 histidine residues to a recombinant protein to be expressed enables efficient purification using a nickel affinity column. By combining the above-mentioned methods, it is possible to produce the glyceroglycolipid lipase of the present invention readily with high yield with high purity in large quantities.

The glyceroglycolipid lipase produced by the method as described above can also be mentioned as a preferable example of the present invention.

Glyceroglycolipid lipase-producing microorganisms refer to microorganisms that essentially inherently have the ability to produce glyceroglycolipid lipases. Glyceroglycolipid lipase-producing microorganisms include microorganisms that accumulate glyceroglycolipid lipases in the cells, microorganisms that secret glyceroglycolipid lipases outside the cells, and the like. When culture supernatants of glyceroglycolipid lipase-producing microorganisms or glyceroglycolipid lipases purified from culture supernatants are to be used, microorganisms that secrete the glyceroglycolipid lipases outside the cells can be used.

A glyceroglycolipid lipase from *Aspergillus japonicus* can be used as the glyceroglycolipid lipase used in the present invention. More preferably, a glyceroglycolipid lipase derived from *Aspergillus japonicus* strain SANK 11298 can be used. The glyceroglycolipid lipase may be derived from *Aspergillus japonicus* itself or a mutant or a modification thereof. Furthermore, it may be a recombinant protein produced from a transformant obtained by introducing a gene encoding a glyceroglycolipid lipase of such a glyceroglycolipid lipase-producing microorganism into a host.

Microorganisms that produce a glyceroglycolipid lipase include, but are not limited to, filamentous fungi of the genus

*Aspergillus*, preferably *Aspergillus japonicus*, more preferably *Aspergillus japonicus* strain SANK 11298 (hereinafter referred to as "strain SANK 11298"). Strain SANK 11298 was separated from soil collected in Gunma Prefecture.

Strain SANK 11298 was inoculated onto three kinds of media (CYA medium, MEA medium, and CY20S medium) to observe mycological properties according to the literature by Klich (Klich, M. A. (2002) Identification of common *Aspergillus* species. The Centraalbureau voor Schimmelcultures, Utrecht, The Netherlands). The compositions of the three kinds of media (CYA medium, MEA medium, and CY20S medium) are as follows.

| CYA medium (Czapek Yeast Extract Agar medium) | |
|---|---|
| $KH_2PO_4$ | 1 g |
| Czapek concentrated solution | 10 ml |
| ($NaNO_3$ 30 g, KCl 5 g, $MgSO_4 \cdot 7H_2O$ 5 g, $FeSO_4 \cdot 7H_2O$ 0.1 g, $CuSO_4 \cdot 5H_2O$ 0.05 g, distilled water 100 ml) | |
| Yeast extract | 5 g |
| Sucrose | 30 g |
| Agar | 15 g |
| Distilled water | 1000 ml |

| MEA medium (Malt Extract Agar medium) | |
|---|---|
| Malt extract | 20 g |
| Peptone | 1 g |
| Glucose | 20 g |
| Agar | 20 g |
| Distilled water | 1000 ml |

| CY20S medium (Czapek Yeast Extract Agar with 20% sucrose medium) | |
|---|---|
| $KH_2PO_4$ | 1 g |
| Czapek concentrated solution | 10 ml |
| Yeast extract | 5 g |
| Sucrose | 200 g |
| Agar | 15 g |
| Distilled water | 1000 ml |

The diameter of colony on CYA medium is 62-64 mm after culturing at 25° C. for 7 days. The colony has radial grooves. The conidiating part is velvety and presents a yellowish brown color (5F4). The mycelium presents a white color. Sclerotium, soluble pigment or exudation is not observed. The back side of the plate presents a pale orange color (5A3). The diameter of colony on MEA medium is 62-65 mm after culturing at 25° C. for 7 days. The conidium is not formed densely. The mycelium presents a white color. Exudation is not observed. There is no color change on the back side of the plate. The diameter of colony on CY20S medium is 58-61 mm after culturing at 25° C. for 7 days. The colony is thick, and the mycelium presents a white color. Conidium or exudate is not observed. The back side of the plate presents a yellowish white color (4A2). The diameter of colony on CYA medium is 13-17 mm after culturing at 37° C. for 7 days. The colony has radial grooves. Soluble pigment is observed, and a pale brown color is presented with a pale red color in the central part. The back side of the plate presents a brown color (7F4) or a grayish brown color (7E3). The colors are indicated according to Kornerup A. & Wanscher J. H.1978. Methuen handbook of colour (3rd. edition). Erye Metuen, London.

The conidial heads are radial. The conidiophore is (100–)300–800(–1200)×3.5–9 μm, smooth, colorless or presents a pale brown color at the tip. The vesicle is (11–)20–39 μm in width and spherical. The aspergilla are monostichous. The phialides are 6–8×3–3.5 and are formed on three quarters or more of the vesicles. The conidium is 3.5–5×3–4 μm in diameter, and spherical or subspherical or often elliptical with acicular surface.

Based upon the above-mentioned mycological properties, strain SANK 11298 is identified as *Aspergillus japonicus* because its properties are consistent with those of *Aspergillus japonicus* as described in the literature by Klich (supra) except for the properties on CY20S medium.

Strain SANK 11298 has been deposited as of Dec. 27, 2006 under Accession No. FERM BP-10753 with International Patent Organism Depositary, National Institute of Advanced Industrial Science and Technology.

Specific properties of a glyceroglycolipid lipase obtained from a glyceroglycolipid lipase-producing microorganism are shown below. However, the properties of the glyceroglycolipid lipase of the present invention are not limited thereto.

The glyceroglycolipid lipase produced by and purified from strain SANK 11298 has the following properties:

1) having a molecular weight of approximately 29,000 as determined by SDS-PAGE;

2) hydrolyzing neutral fat, lecithin, and glyceroglycolipid at pH 6.0;

3) having a glyceroglycolipid degradation activity at least 10-fold higher than a lecithin degradation activity at pH ranging from 3.6 to 8.9;

4) having a relative degradation activity of at least 80% or more for glyceroglycolipid at pH ranging from 4.1 to 7.7;

5) having a relative degradation activity of at least 80% or more for lecithin at pH ranging from 5.1 to 7.1;

6) not having the hydrolytic activity of 5) at a temperature of 80° C. or higher;

7) having a relative residual degradation activity of 75% or more for glyceroglycolipid at pH ranging from 4.1 to 10.7.

Fatty acid-liberating activities for glyceroglycolipid DGDG (hereinafter referred to as "DGDG degradation activity") and fatty acid-liberating activities for soybean lecithin (hereinafter referred to as "lecithin degradation activity") were measured at various pH values. Comparison of the relative lecithin degradation activities observed using the enzyme of the present invention with those observed using LIPOFAN F™ (Novozymes Japan Ltd.), a lipase widely used in the baking industry, is shown below defining, as 100%, the DGDG degradation activities at the respective pH values. The soybean-derived lecithin was purchased from Tsuji Oil Mill Co., Ltd. Hereinafter, lecithin refers to soybean-derived lecithin.

| Enzyme of the invention (Glyceroglycolipid lipase G-2) | | |
|---|---|---|
| pH | DGDG degradation activity | Lecithin degradation activity |
| 3.6 | 100 | 2.6 |
| 4.1 | 100 | 4.6 |
| 4.9 | 100 | 5.9 |
| 5.9 | 100 | 6.1 |
| 6.7 | 100 | 5.3 |
| 7.7 | 100 | 4.6 |
| 8.1 | 100 | 6.8 |
| 8.9 | 100 | 8.5 |

| Lipopan F purified enzyme | | |
|---|---|---|
| pH | DGDG degradation activity | Lecithin degradation activity |
| 3.4 | 100 | 41.4 |
| 4.1 | 100 | 142 |
| 5.1 | 100 | 220 |
| 5.9 | 100 | 186 |
| 6.9 | 100 | 171 |
| 7.7 | 100 | 118 |
| 8.5 | 100 | 118 |
| 9.2 | 100 | 110 |
| 9.9 | 100 | 106 |

As can be seen from the above, the enzyme of the present invention has a glyceroglycolipid degradation activity at least 10-fold higher than a lecithin degradation activity at pH ranging from 3.6 to 8.9. On the other hand, a commercially available lipase LIPOFAN F™ has a glyceroglycolipid degradation activity at most 3-fold higher than a lecithin degradation activity at pH ranging from 3.4 to 9.9, and the glyceroglycolipid degradation activity is equivalent to or lower than the lecithin degradation activity at pH ranging from pH 4.1 to pH 9.9.

The glyceroglycolipid lipase produced by and purified from strain SANK 11298 has the partial amino acid sequence of SEQ ID NO: 3. The sequence is shown from the N terminus.

Based on the above, the properties of the glyceroglycolipid lipase of the present invention include, but are not limited to, the following:

1) having a molecular weight of approximately 29,000 as determined by SDS-PAGE;

2) hydrolyzing neutral fat, lecithin, and glyceroglycolipid at pH 6.0;

3) having a glyceroglycolipid degradation activity at least 10-fold higher than a lecithin degradation activity at pH ranging from 3.6 to 8.9;

4) having a relative degradation activity of at least 80% or more for glyceroglycolipid at pH ranging from 4.1 to 7.7;

5) having a relative degradation activity of at least 80% or more for lecithin at pH ranging from 5.1 to 7.1;

6) not having the hydrolytic activity of 5) at a temperature of 80° C. or higher;

7) having a relative residual degradation activity of 75% or more for glyceroglycolipid at pH ranging from 4.1 to 10.7.

A method of producing the glyceroglycolipid lipase of the present invention is also included in the present invention.

A glyceroglycolipid lipase can be produced by culturing a glyceroglycolipid lipase-producing microorganism including strain SANK 11298 in a medium. For example, shaking culture is conducted at 100-250 rpm for 1-15 days at 16-45° C. in a medium containing 0.1-5.0% glucose (Wako Pure Chemical Industries, Ltd.), 0.1-5.0% yeast extract (Difco Laboratories), 0.1-5.0% Casamino Acids (Difco Laboratories), 0.1-5.0% TWEEN 80® (Sigma-Aldrich Japan Co., Ltd.), 0.01-1.0% dipotassium hydrogenphosphate, 0.005-1.0% magnesium sulfate, and 0.05-5.0% ground sesame.

EXAMPLES

Examples and Test Examples are given below. However, the scope of the present invention is not limited thereto.

Example 1

Purification of Glyceroglycolipid Lipase from Strain SANK 11298

1) Preparation of Crude Enzyme Solution

Cells of strain SANK 11298 were inoculated into 100 ml of a sterilized medium of the following composition contained in a 500-ml Erlenmeyer flask, and cultured with shaking at 170 rpm at 26° C. for 4 days.

| Medium composition | |
|---|---|
| Glucose | 20 g |
| Yeast extract | 10 g |
| Casamino Acids | 10 g |
| Ground sesame | 20 g |
| Tween 80 | 10 g |
| Dipotassium hydrogenphosphate | 0.1 g |
| Magnesium sulfate | 0.05 g |

It was adjusted to 1,000 ml with pure water.

After completing the culture, centrifugation was carried out at 10,000×G and at 4° C. for 10 minutes. The resulting supernatant was used as a crude enzyme solution.

2) Method of Measuring Enzymatic Activity

The hydrolytic activity of the glyceroglycolipid lipase was measured as follows:

1. Using DGDG as Substrate (DGDG Degradation Activity)

A fraction extracted and purified from Nisshin Flour weak wheat flour (Nisshin Flour Milling Inc.), which gives a single spot on TLC and results similar to those for SIGMA D4651-10MG digalactosyl diglyceride in mass spectrometry, was used as DGDG below.

200 mg of DGDG was dissolved in 10 ml of 4% TRITON X-100® to obtain a 2% DGDG solution. 30 μA of the enzyme solution was added to a mixture of 210 μl of 2% DGDG solution and 30 μl of 400 mM MOPS buffer (pH 6) which had been incubated at 37° C. for 5 minutes. The mixture was adequately stirred and then incubated at 37° C. for 10 minutes. The enzymatic reaction was stopped by adding 30 μl of 1N hydrochloric acid. The enzyme solution was diluted with 1% Triton X-100 before use.

2. Using Lecithin or LPC as Substrate (Lecithin Degradation Activity)

200 mg of lecithin (SLP-White, Tsuji Oil Mill Co., Ltd.) was dissolved in 10 ml of 4% TRITON X-100® to obtain a 2% lecithin solution. 150 μl of the enzyme solution was added to a mixture of 500 μl of 2% lecithin solution and 250 μl of 200 mM MOPS buffer (pH 6) which had been incubated at 37° C. for 5 minutes. The mixture was adequately stirred and then incubated at 37° C. for 10 minutes. The enzymatic reaction was stopped by adding 100 μl of 1N hydrochloric acid. The enzyme solution was diluted with 1% TRITON X-100® before use. Conditions similar to the above were also used when LPC was used as a substrate.

3. Using Olive Oil as Substrate (Neutral Fat Degradation Activity)

10 ml of water was added to 200 mg of olive oil (Nacalai Tesque, Inc.) and 100 mg of gum arabic (Wako Pure Chemical Industries, Ltd.), and the mixture was emulsified using a blender (Nippon Seiki Co., Ltd.) at 10,000 rpm for 1 minute. 40 µl of the enzyme solution was added to a mixture of 200 µl of the above solution, 100 µl of 200 mM MOPS buffer (pH 6) and 20 µl of 100 mM calcium chloride solution which had been incubated at 37° C. for 5 minutes. The mixture was adequately stirred and then incubated at 37° C. for 10 minutes. The enzymatic reaction was stopped by adding 40 µl of 1N hydrochloric acid. 400 µl of 4% Triton X-100 was added to this mixture to dissolve liberated free fatty acid.

4. Quantification of Free Fatty Acid

The liberated free fatty acid resulting from the enzymatic reaction was quantified using NEFA (Kyowa Medex Co., Ltd.). 3 ml of NEFA solution was added to 30 µl of the reaction mixture obtained in 1, 2, or 3 above under shaded conditions, and the mixture was reacted at 37° C. for 10 minutes. The absorbance of this mixture was measured at 660 nm. One unit of DGDG degradation activity was defined as the amount of enzyme that liberates 1 µmol of free fatty acid from DGDG in 1 minute. One unit of lecithin degradation activity was defined as the amount of enzyme that liberates 1 µmol of free fatty acid from lecithin in 1 minute. One unit of neutral fat degradation activity was defined as the amount of enzyme that liberates 1 µmol of free fatty acid from olive oil in 1 minute.

3) Preparation of Purified Enzyme Solution

Ammonium sulfate (Wako Pure Chemical Industries, Ltd.) was added to 500 ml of the crude enzyme solution obtained in 1), and the final concentration was adjusted to 1M. This mixture was applied and adsorbed to a Toyopearl Butyl 650M (Tosoh Corporation) column (2.2 cm in diameter×20 cm in length) which had been equilibrated with 1M ammonium sulfate. The column was washed extensively with 1M ammonium sulfate. Then, 600 ml of a linear gradient from 1 M ammonium sulfate to 0 M ammonium sulfate with 0.1% TWEEN 80® was prepared to elute the components adsorbed to the column. The lecithin degradation activity was eluted in a fraction (120 ml) at 0 M-0.2 M ammonium sulfate concentration. This fraction was used as a partially purified enzyme fraction.

120 ml of the obtained active fraction was dialyzed 3 times against 4,000 ml of 10 mM Tris-HCl/0.1% TWEEN 80® buffer (pH 8) for 12 hours each, and then applied and adsorbed to a Toyopearl DEAE 650M (Tosoh Corporation) column (2.2 cm in diameter×20 cm in length) which had been equilibrated with 10 mM Tris-HCl/0.1% TWEEN 80® buffer (pH 8). The column was washed extensively with 10 mM Tris-HCl/0.1% TWEEN 80® buffer (pH 8). Then, a linear gradient of 0-1.0 M sodium chloride in 10 mM Tris-HCl/0.1% TWEEN 80® buffer (pH 8) was prepared to elute the components adsorbed to the column. The lecithin degradation activity was eluted in a fraction (120 ml) at 0.42 M-0.59 M sodium chloride concentration.

40 ml of the obtained active fraction was concentrated and applied to a HiLoad Sephadex 200 pg (GE Healthcare Biosciences Corp.) column (16 mm in diameter×60 cm) which had been equilibrated with 10 mM Tris-HCl buffer (pH 7.5) containing 0.15M sodium chloride, and was then eluted with 10 mM Tris-HCl buffer (pH 7.5) containing 0.15M sodium chloride. The lecithin degradation activity was eluted in fractions at 60 ml-67.5 ml and 81 ml-90 ml elution volumes. The former was used as a glyceroglycolipid lipase G-1, and the latter was used as a glyceroglycolipid lipase G-2.

These fractions were used as purified enzyme solutions.

4) Measurement of Molecular Weight of Purified Enzyme

The molecular weights of the purified enzymes were determined by SDS-PAGE using a 12.5% polyacrylamide gel (see Laemmli, U. K., Nature, 227, 680 (1970)). The following proteins were used as standard proteins: a. phosphorylase, MW 97,000: b. albumin, MW 66,000: c. ovalbumin, MW 45,000: d. carbonic anhydrase, MW 30,000: e. trypsin inhibitor, MW 20,100: f. α-lactalbumin, MW 14,400. Both the glyceroglycolipid lipase G-1 and the glyceroglycolipid lipase G-2 exhibited single bands of molecular weights of approximately 29,000.

5) Measurement of Isoelectric Point

Measurement was conducted using PhastGel IEF 3-9 (Amersham Biosciences Corp.). The glyceroglycolipid lipase G-2 exhibited pI of around 4.5. The following proteins were used as standard proteins: a. amylglucosidase, pI 3.50: b. trypsin inhibitor, pI 4.55: c. β-lactoglobulin A, pI 5.20: d. carbonic anhydrase B (bovine), pI 5.85: e. carbonic anhydrase B (human), pI 6.55: f. myoglobin, acidic band, pI 6.85: g. myoglobin, basic band, pI 7.35: h. lentil lectin, acidic, pI 8.15: i. lentil lectin, neutral, pI 8.45: j. lentil lectin, basic, pI 8.65: k. trypsinogen, pI 9.30.

Example 2

Purification of Glyceroglycolipid Lipase from Lipopan F 1M ammonium sulfate solution was added to Lipopan F (20 g) to elute the enzyme, and the precipitate was then removed. The supernatant was applied and adsorbed to a Toyopearl Butyl 650M (Tosoh Corporation) column (2.2 cm in diameter×20 cm in length) which had been equilibrated with 1M ammonium sulfate. The column was washed extensively with 1M ammonium sulfate. Then, 600 ml of a linear gradient from 1 M ammonium sulfate to 0 M ammonium sulfate with 0.1% TWEEN 80® was prepared to elute the components adsorbed to the column. The lecithin degradation activity was eluted in a fraction (120 ml) at 0 M-0.2 M ammonium sulfate concentration. This fraction was used as a Lipopan F partially purified enzyme fraction.

120 ml of the obtained active fraction was dialyzed 3 times against 4,000 ml of 10 mM Tris-HCl/0.1% TWEEN 80® buffer (pH 8) for 12 hours each, and was then applied and adsorbed to a Toyopearl DEAE 650M (Tosoh Corporation) column (2.2 cm in diameter×20 cm in length) which had been equilibrated with 10 mM Tris-HCl/0.1% Tween 80 buffer (pH 8). The column was washed extensively with 10 mM Tris-HCl/0.1% TWEEN 80® buffer (pH 8). Then, a linear gradient of 0-1.0 M sodium chloride in 10 mM Tris-HCl/0.1% TWEEN 80® buffer (pH 8) was prepared to elute the components adsorbed to the column. The lecithin degradation activity was eluted in a fraction (120 ml) at 0.42 M-0.59 M sodium chloride concentration.

This fraction was used as a Lipopan F purified enzyme.

Example 3

Determination of N-Terminal Amino Acid Sequence of Glyceroglycolipid Lipase Derived from Strain SANK 11298

The purified enzyme was applied to SDS-PAGE by the method as shown in Example 1. 4) and then blotted onto a PVDF membrane. The amino acid sequence was analyzed using an amino acid sequence analyzer (Procise cLC, Applied Biosystems Inc.). The resulting partial amino acid sequence is indicated from the amino terminal side (SEQ ID NO: 3).

Example 3

Identification of DNA Encoding the Glyceroglycolipid Lipase of Strain SANK 11298

1) Purification of Total RNA

Strain SANK 11298 was precultured at 26° C. for 2 days in 20 ml of a liquid medium (2% polypeptone (Wako Pure Chemical Industries, Ltd.), 0.5% yeast extract, 0.02% dipotassium hydrogenphosphate, 0.05% magnesium sulfate). The preculture was then inoculated at a ratio of 1% into a liquid medium (2% glucose, 1% yeast extract, 1% Casamino Acids, 2% ground sesame, 1% TWEEN 80®, 0.1% dipotassium hydrogenphosphate, 0.02% magnesium sulfate) and cultured at 26° C. for 4 days. The cultured cells were collected by aspiration and transferred to a mortar (autoclaved) which had been cooled at −80° C. The cells were crushed and powdered using a pestle while adding liquid nitrogen. Total RNA was purified from the completely powdered cells using RNeasy Plant MiniKit (Qiagen GmbH). 50 µl of a solution at a concentration of 660 ng/µg was obtained.

2) Analysis of Glyceroglycolipid Lipase Gene

The gene sequence was analyzed by the 5' RACE method and the 3' RACE method. Specifically, PCR was conducted using 5' RACE System and 3' RACE System (both from Invitrogen Corp.) and EX Taq™ (Takara Bio Inc.) as a polymerase. The PCR primers of SEQ ID NOS: 4 and 5 for 5' gene sequence amplification and of SEQ ID NOS: 6 and 7 for 3' gene sequence amplification were used. Amplification was conducted using PCR cycles as follows: 94° C. for 5 minutes, (94° C. for 30 seconds, 55° C. for 30 seconds, 72° C. for 2 minutes and 30 seconds)×30, 72° C. for 10 minutes, 4° C. DNA of approximately 1,000 bp in length was amplified for the 5' gene sequence, and DNA of approximately 1,200 bp in length was amplified for the 3' gene sequence.

Each PCR product was subjected to agarose gel electrophoresis, and then purified using Qiaquick Gel Extraction Kit (Qiagen GmbH). The purified product was ligated to a vector using TOPO™ TA cloning kit (Invitrogen Corp.), and was used for transformation. After the transformed *Escherichia coli* cells were cultured on an agar medium (LB/Agar, Wako Pure Chemical Industries, Ltd.) at 37° C. overnight, grown colonies were cultured in a liquid medium (LB broth, Wako Pure Chemical Industries, Ltd.) at 37° C. overnight. Plasmids were purified from the grown *Escherichia coli* cells using Qiaprep Spin Miniprep Kit (Qiagen GmbH) and subjected to DNA sequence analysis. The results of the DNA sequence analysis are shown in SEQ ID NO: 1. The amino acid sequence deduced from the DNA sequence is shown in SEQ ID NO: 2.

Test Example 1

Various Properties of Purified Enzyme Solution of Glyceroglycolipid Lipase Derived from Strain SANK 11298

The purified enzyme solutions obtained in Example 1.3) were subjected to activity measurements.

1) Substrate Selectivity

2% solutions were prepared for respective substrates, and measurements were conducted according to the method of Example 1. 2) using the glyceroglycolipid lipase G-2 as shown in Example 1. 3) or the Lipopan F purified enzyme as shown in Example 2 as an enzyme. Relative activities are shown defining the DGDG degradation activity as 100%. Lecithin represents SLP-White. LPC was derived from soybean, and purchased from Sigma-Aldrich Japan Co., Ltd.

| Substrate | G-2 | Lipopan F unpurified enzyme | Lipopan F purified enzyme |
|---|---|---|---|
| DGDG | 100 | 100 | 100 |
| Lecithin | 6.1 | 229 | 186 |
| LPC | 0.5 | 9.9 | 0.7 |
| Olive oil | 28.3 | 27.4 | ND |

2) pH/Activity

1. Using DGDG as Substrate

Figure 2:
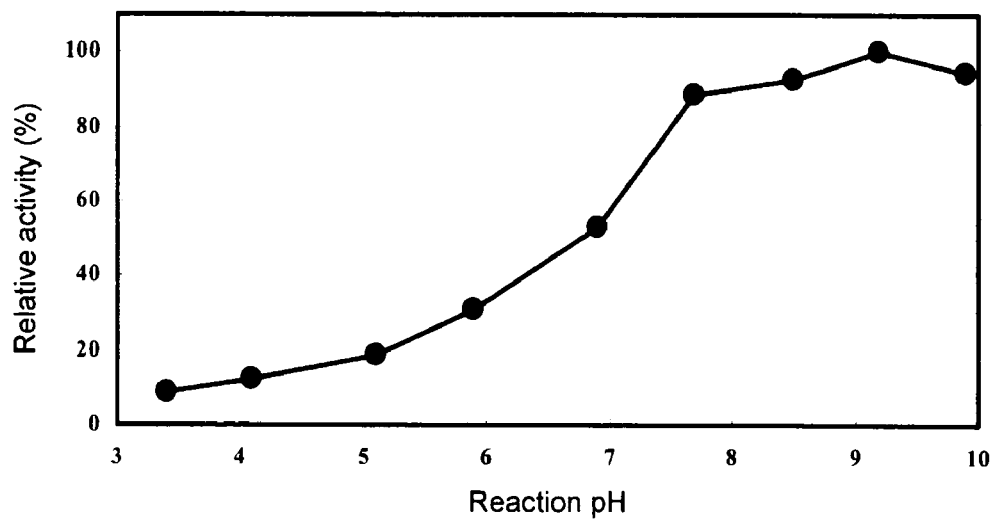
FIG. 2: pH/activity of the Lipopan F purified enzyme using DGDG as a substrate.

Activities measurements were conducted according to the method as shown in Example 1. 2) 1. The glyceroglycolipid lipase G-2 as shown in Example 1. 3) or the Lipopan F purified enzyme as shown in Example 2 was used as an enzyme. Acetate buffer (pH 3-6), MOPS buffer (pH 6-8), or Atkins-Pantin buffer (pH 8-11) was used as a buffer. The relative degradation activities of both enzymes at the respective pH values are described below. The results obtained using the glyceroglycolipid lipase G-2 are shown in FIG. 1, and the results for the Lipopan F purified enzyme are shown in FIG. 2.

| pH/activity (FIGS. 1 and 2) | | | |
|---|---|---|---|
| G-2 | | Lipopan F purified enzyme | |
| pH | Relative activity (%) | pH | Relative activity (%) |
| 3.6 | 78.2 | 3.4 | 8.7 |
| 4.1 | 87.0 | 4.1 | 12.3 |
| 4.9 | 96.4 | 5.1 | 18.4 |
| 5.9 | 99.3 | 5.9 | 31.1 |
| 6.7 | 100 | 6.9 | 52.7 |
| 7.7 | 90.5 | 7.7 | 88.2 |
| 8.1 | 64.1 | 8.5 | 92.7 |
| 8.9 | 43.7 | 9.2 | 100 |
| 9.6 | 13.5 | 9.9 | 94.3 |

In the present invention, the pH at which a relative activity of 80% or more is retained is defined as the optimum pH. Thus, the optimum pH of the glyceroglycolipid lipase G-2 of the present invention is pH 4.1-7.7. The optimum pH of the Lipopan F purified enzyme is pH 7.7-9.9. The pH values at which a relative activity of 90% or more is retained are 4.9-7.7 for the glyceroglycolipid lipase G-2 and 8.5-9.9 for the Lipopan F purified enzyme.

2. Using Lecithin as Substrate

Figure 3:
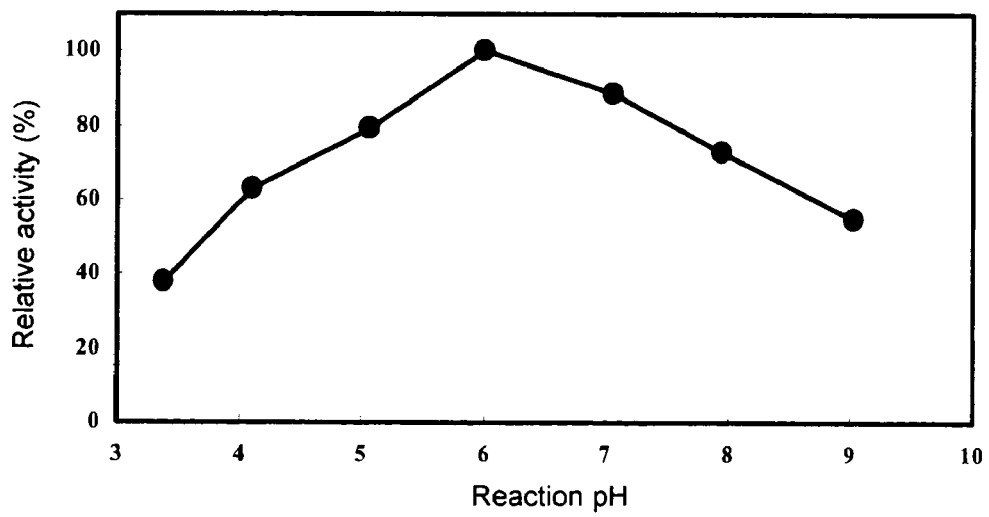
FIG. 3: pH/activity of the purified glyceroglycolipid lipase G-1 derived from strain SANK 11298 using lecithin as a substrate.
Figure 4:
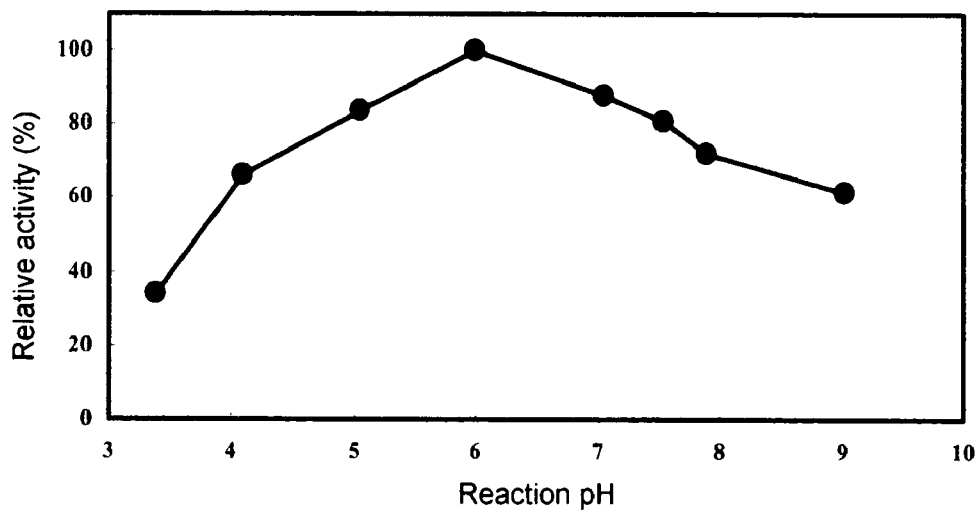
FIG. 4: pH/activity of the purified glyceroglycolipid lipase G-2 derived from strain SANK 11298 using lecithin as a substrate.

Activity measurements were carried out according to the method as shown in Example 1. 2) 2. The glyceroglycolipid lipase G-1 or the glyceroglycolipid lipase G-2 as shown in Example 1. 3) was used as an enzyme. The following buffers were used: acetic acid/sodium acetate buffer (pH 3.4-pH 6.1); MOPS buffer (pH 6.0-pH 8.0); Tris-HCl buffer (pH 7.5-pH 9.0). The relative degradation activities of both enzymes at the respective pH values are described below. The results obtained using the glyceroglycolipid lipase G-1 are shown in FIG. 3, and the results for the glyceroglycolipid lipase G-2 are shown in FIG. 4.

| pH/activity (FIGS. 3 and 4) | | |
|---|---|---|
| | Relative activity (%) | |
| pH | G-1 | G-2 |
| 3.4 | 37.9 | 40.1 |
| 4.1 | 62.9 | 67.6 |
| 5.1 | 79.3 | 94.2 |
| 6.0 | 100 | 100 |
| 7.1 | 88.3 | 93.9 |
| 8.0 | 72.9 | 71.8 |
| 9.0 | 55.0 | 60.3 |

In the present invention, the pH at which a relative activity of 80% or more is retained is defined as the optimum pH. Thus, the optimum pH of the glyceroglycolipid lipase G-1 of the present invention using lecithin as a substrate is pH 6.0-7.1. The optimum pH of the glyceroglycolipid lipase G-2 is pH 5.1-7.1.

3) pH/Stability

1. Using DGDG as Substrate

Figure 5:
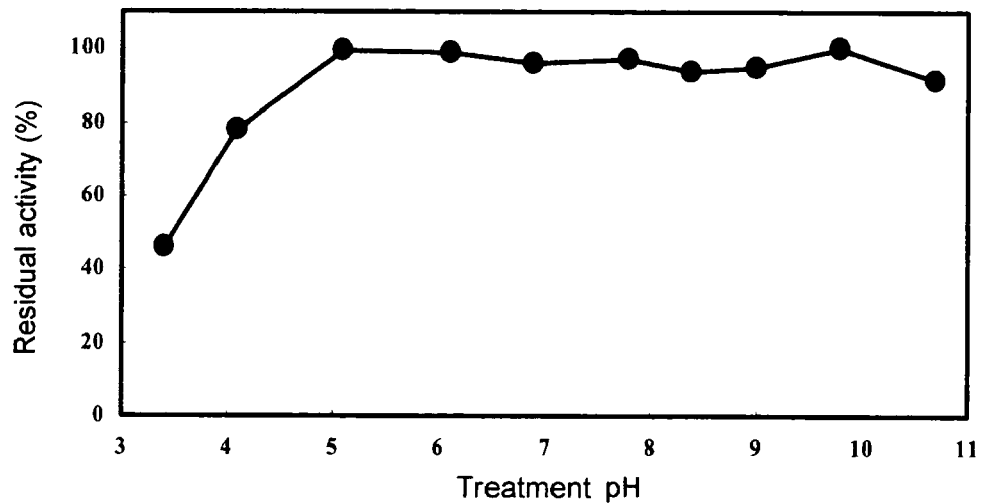
FIG. 5: pH/stability of the purified glyceroglycolipid lipase G-2 derived from strain SANK 11298 using DGDG as a substrate.
Figure 6:
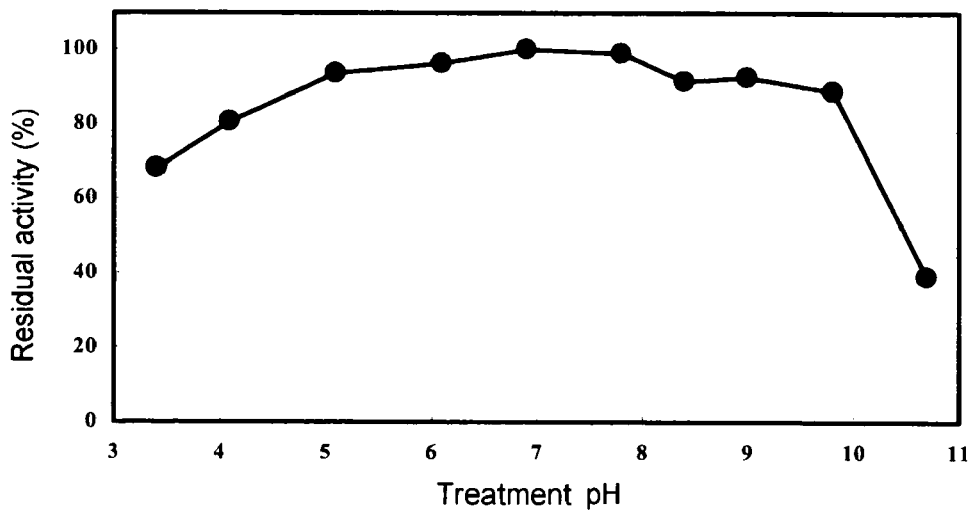
FIG. 6: pH/stability of the Lipopan F purified enzyme using DGDG as a substrate.

A mixture of 10 μl of the glyceroglycolipid lipase G-2 as shown in Example 1. 3) or the Lipopan F purified enzyme as shown in Example 2 as an enzyme, and 190 μl of 20 mM buffer/1% TRITON X-100® solution was incubated at 37° C. for 30 minutes and then immediately cooled on ice. Acetate buffer (pH 3-6), MOPS buffer (pH 6-8), or Atkins-Pantin buffer (pH 8-11) was used as a buffer. Relative residual degradation activity was measured according to the method of Example 1. 2) 1 immediately after each warmed enzyme solution was diluted 10-fold with water. Relative residual degradation activities of the enzymes at respective pH values are described below as relative values defining, as 100%, the residual degradation activity under pH conditions that resulted in the highest activity. The results obtained using the glyceroglycolipid lipase G-2 are shown in FIG. 5, and the results for the Lipopan F purified enzyme are shown in FIG. 6.

| pH/stability (FIGS. 5 and 6) | | |
|---|---|---|
| | Relative residual degradation activity (%) | |
| pH | G-2 | Lipopan F purified enzyme |
| 3.4 | 45.7 | 68.1 |
| 4.1 | 77.8 | 81.0 |
| 5.1 | 99.6 | 93.7 |
| 6.1 | 99.0 | 96.3 |
| 6.9 | 96.3 | 100 |
| 7.8 | 97.4 | 99.0 |
| 8.4 | 93.5 | 91.8 |
| 9.0 | 94.6 | 92.5 |
| 9.8 | 100 | 89.1 |
| 10.7 | 91.5 | 39.0 |

In the present invention, the pH at which a relative residual degradation activity of 80% or more is retained is defined as the stable pH. Thus, the stable pH of the glyceroglycolipid lipase G-2 of the present invention is pH 5.1-10.7. The stable pH of the Lipopan F purified enzyme is pH 4.1-9.8.

2. Using Lecithin as Substrate

Figure 7:
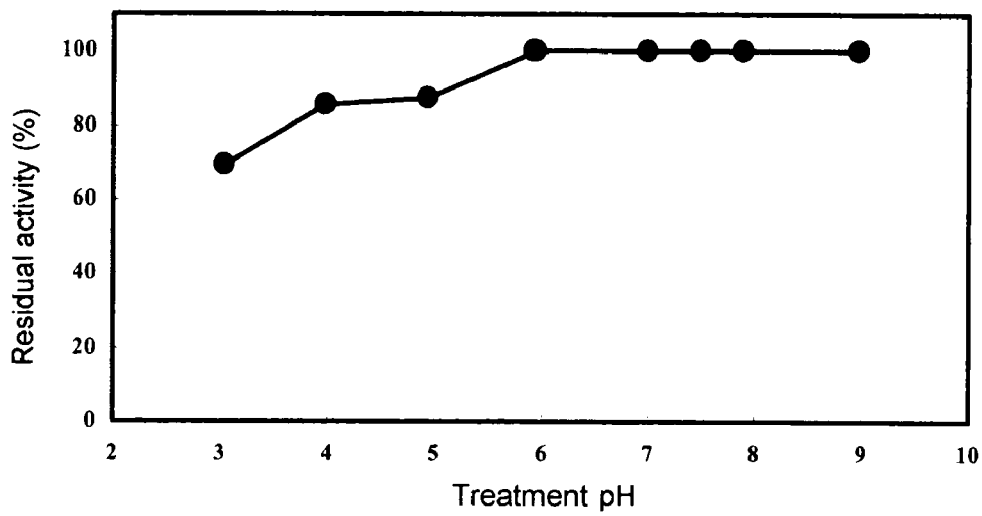
FIG. 7: pH/stability of the purified glyceroglycolipid lipase G-2 derived from strain SANK 11298 using lecithin as a substrate.

50 μl of one of 200 mM buffers at pH values as described below was added to 50 μl of the glyceroglycolipid lipase G-2 as shown in Example 1.3, and the mixture was incubated at 37° C. for 30 minutes. The following buffers were used: acetic acid/sodium acetate buffer (pH 3.0-pH 6.0); MOPS buffer (pH 5.9-pH 7.9); Tris-HCl buffer (pH 7.6-pH 9.0). Relative residual degradation activity was measured according to the method of Example 1. 2) 1. immediately after each warmed enzyme solution was diluted 10-fold with water. Relative residual degradation activities of the enzymes at respective pH values are described below as relative values defining, as 100%, the residual degradation activity under pH conditions that resulted in the highest activity. The results are also shown in FIG. 7.

| pH/stability (FIG. 7) | |
|---|---|
| pH | Relative residual degradation activity (%) |
| 3.0 | 69.4 |
| 4.0 | 85.4 |
| 4.9 | 87.1 |
| 6.0 | 100 |
| 7.0 | 100 |
| 7.5 | 100 |
| 7.9 | 100 |
| 9.0 | 100 |

In the present invention, the pH at which a relative residual degradation activity of 80% or more is retained is defined as the stable pH. Thus, the stable pH of the glyceroglycolipid lipase G-2 of the present invention using lecithin as a substrate is pH 4.0-9.0.

4) Temperature/Activity

1. Using DGDG as Substrate

Figure 8:
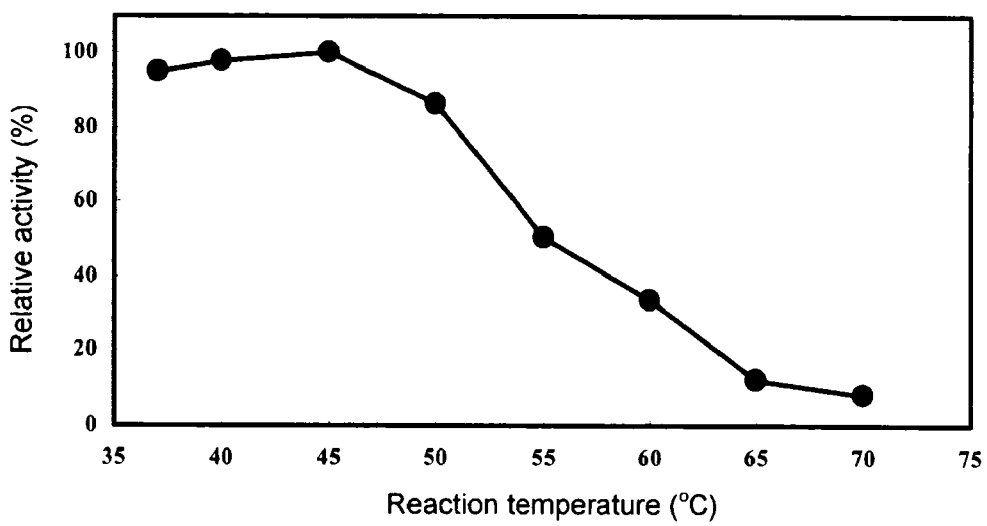
FIG. 8: Temperature/activity of the purified glyceroglycolipid lipase G-2 derived from strain SANK 11298 using DGDG as a substrate.
Figure 9:
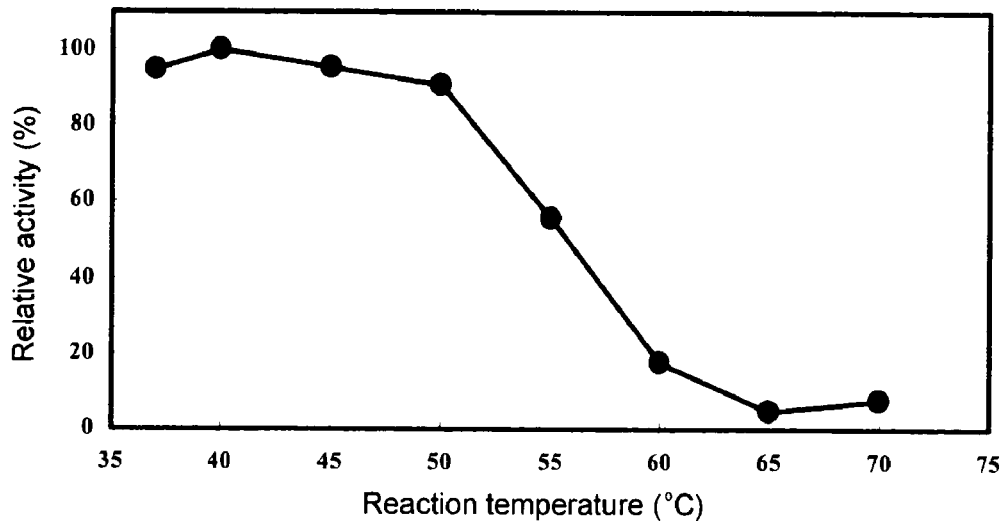
FIG. 9: Temperature/activity of the Lipopan F purified enzyme using DGDG as a substrate.

A temperature/activity in MOPS buffer (pH 6) was measured. The glyceroglycolipid lipase G-2 as shown in Example 1. 3) or the Lipopan F purified enzyme as shown in Example 2 was used as an enzyme. The measurement method was in accordance with the method as shown in Example 1. 2) 1. The relative degradation activities of both enzymes at respective temperatures are described below. The results obtained using the glyceroglycolipid lipase G-2 are shown in FIG. 8, and the results for the Lipopan F purified enzyme are shown in FIG. 9.

| Temperature/activity (FIGS. 8 and 9) | | |
|---|---|---|
| | Relative activity (%) | |
| Temperature (° C.) | G-2 | Lipopan F purified enzyme |
| 37 | 95.1 | 94.9 |
| 40 | 97.7 | 100 |
| 45 | 100 | 95.6 |
| 50 | 86.1 | 90.5 |
| 55 | 50.4 | 55.5 |
| 60 | 33.5 | 17.3 |
| 65 | 12.1 | 4.8 |
| 70 | 8.2 | 7.6 |

In the present invention, the temperature at which a relative activity of 80% or more is retained is defined as the optimal temperature. Thus, the optimum temperature of the glyceroglycolipid lipase G-2 of the present invention using DGDG as a substrate is 37-50° C. This is also applicable to the Lipopan F purified enzyme.

2. Using Lecithin as Substrate

Figure 10:
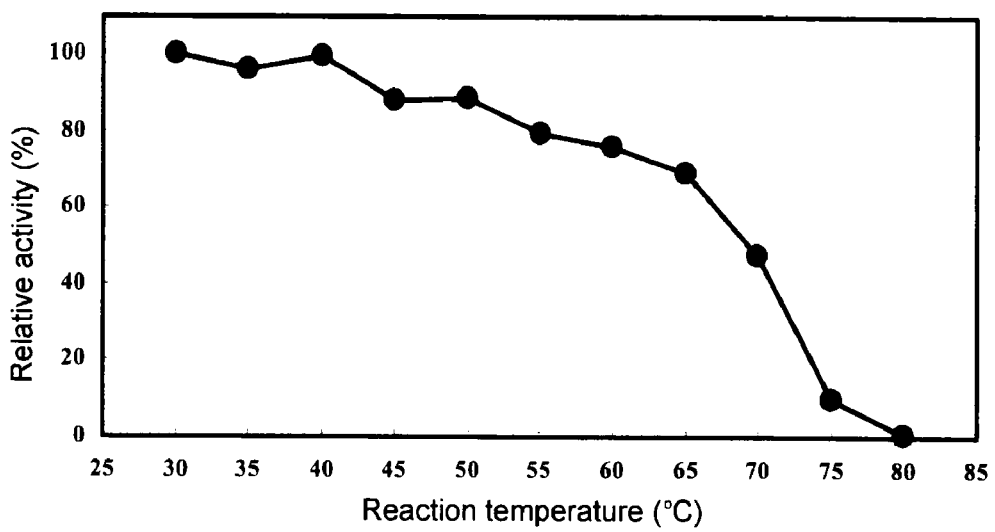
FIG. 10: Temperature/activity of the purified glyceroglycolipid lipase G-1 derived from strain SANK 11298 using lecithin as a substrate.
Figure 11:
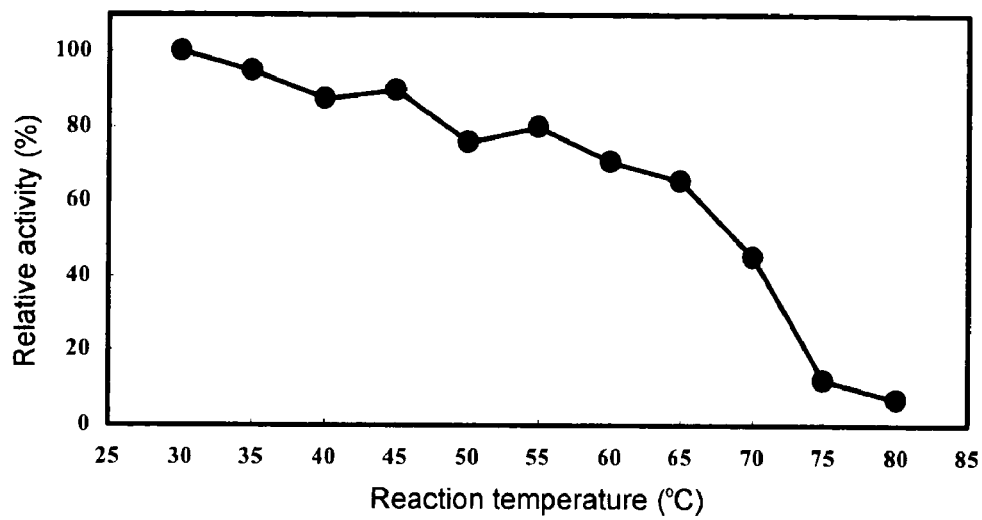
FIG. 11: Temperature/activity of the purified glyceroglycolipid lipase G-2 derived from strain SANK 11298 using lecithin as a substrate.

A temperature/activity in MOPS buffer (pH 6) was measured. The glyceroglycolipid lipase G-1 or the glyceroglycolipid lipase G-2 as shown in Example 1. 3) was used as an enzyme. The measurement method was in accordance with the method as shown in Example 1. 2) 2. The relative degradation activities of both enzymes at respective temperatures are described below. The results obtained using the glyceroglycolipid lipase G-1 are shown in FIG. 10, and the results for the glyceroglycolipid lipase G-2 are shown in FIG. 11.

| Temperature/activity (FIGS. 10 and 11) | | |
|---|---|---|
| Temperature | Relative activity (%) | |
| (° C.) | G-1 | G-2 |
| 30 | 100 | 100 |
| 35 | 96.2 | 94.7 |
| 40 | 99.5 | 87.6 |
| 45 | 88.0 | 90.0 |
| 50 | 88.5 | 75.6 |
| 55 | 79.3 | 79.9 |
| 60 | 76.0 | 70.8 |
| 65 | 68.8 | 65.6 |
| 70 | 47.6 | 45.4 |
| 75 | 10.1 | 12.4 |
| 80 | 0.5 | 6.7 |

In the present invention, the temperature at which a relative activity of 80% or more is retained is defined as the optimal temperature. Thus, the optimal temperature of the glyceroglycolipid lipase G-1 using lecithin as a substrate is 30-50° C. The optimal temperature of the glyceroglycolipid lipase G-2 is 30-45° C.

5) Temperature/Stability

1. Using DGDG as Substrate

Figure 12:
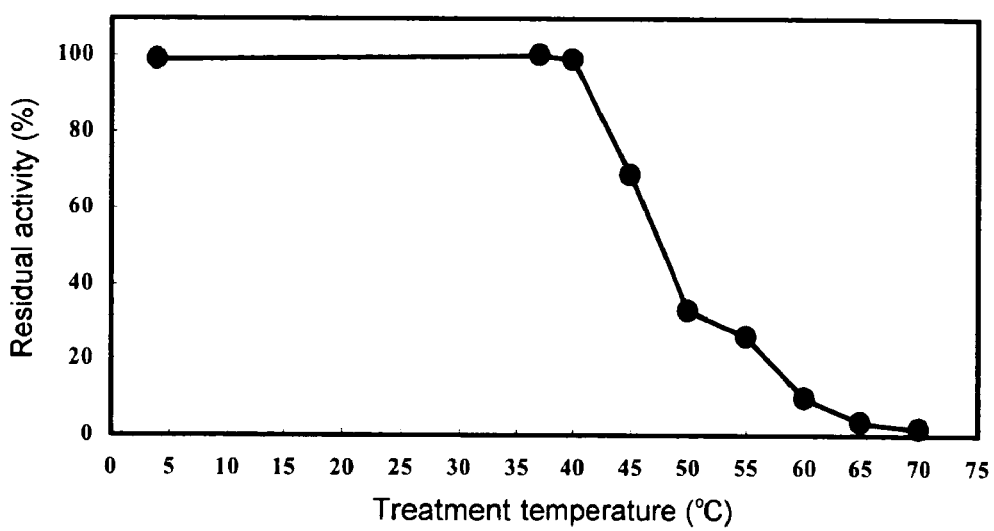
FIG. 12: Temperature/stability of the purified glyceroglycolipid lipase G-2 derived from strain SANK 11298 using DGDG as a substrate.
Figure 13:
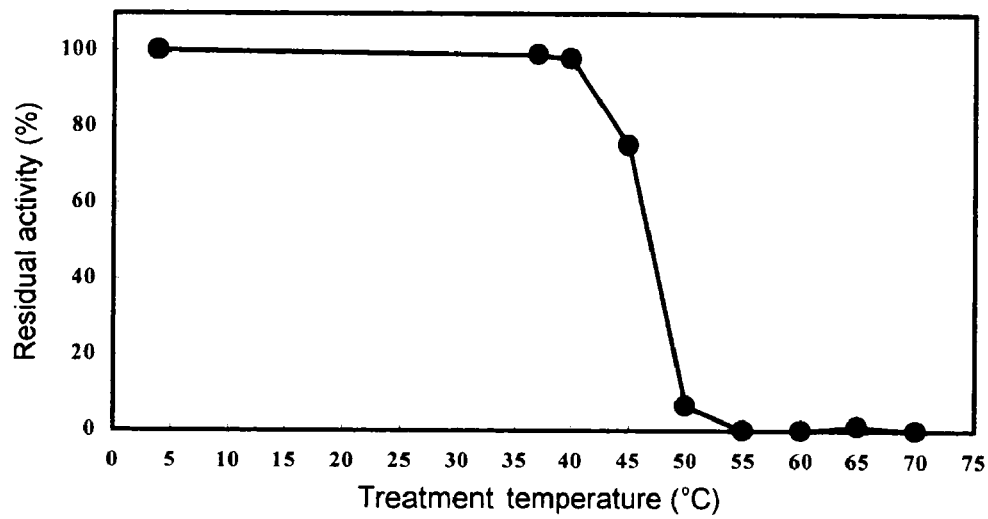
FIG. 13: Temperature/stability of the Lipopan F purified enzyme using DGDG as a substrate.

50 µl of a purified enzyme solution was added to 37.5 µl of 400 mM MOPS buffer (pH 6) and 62.5 µl of 1% TRITON X-100® solution which had been maintained at the treatment temperature. The mixture was stirred to homogeneity, incubated for 30 minutes, and then immediately cooled on ice. The glyceroglycolipid lipase G-2 as shown in Example 1. 3) or the Lipopan F purified enzyme as shown in Example 2 was used as an enzyme. The measurement method was in accordance with the method as shown in Example 1. 2) 1. Relative residual degradation activities of the enzymes at respective temperatures are described below as relative values defining, as 100%, the residual degradation activity under temperature conditions that resulted in the highest activity. The results obtained using the glyceroglycolipid lipase G-2 are shown in FIG. 12, and the results for the Lipopan F purified enzyme are shown in FIG. 13.

| Temperature/stability (FIGS. 12 and 13) | | |
|---|---|---|
| | Relative residual activity (%) | |
| Temperature (° C.) | G-2 | Lipopan F purified enzyme |
| 4 | 99.0 | 100 |
| 37 | 100 | 99.4 |
| 40 | 99.0 | 98.1 |
| 45 | 68.3 | 75.2 |
| 50 | 32.8 | 6.5 |
| 55 | 26.1 | 0.1 |
| 60 | 9.6 | 0.0 |
| 65 | 3.2 | 1.2 |
| 70 | 1.9 | 0.0 |

In the present invention, the temperature at which a relative residual activity of 80% or more is retained is defined as the stable temperature. Thus, the stable temperature of the glyceroglycolipid lipase G-2 of the present invention using DGDG as a substrate is 4-40° C. This is also applicable to the Lipopan F purified enzyme.

2. Using Lecithin as Substrate

Figure 14:
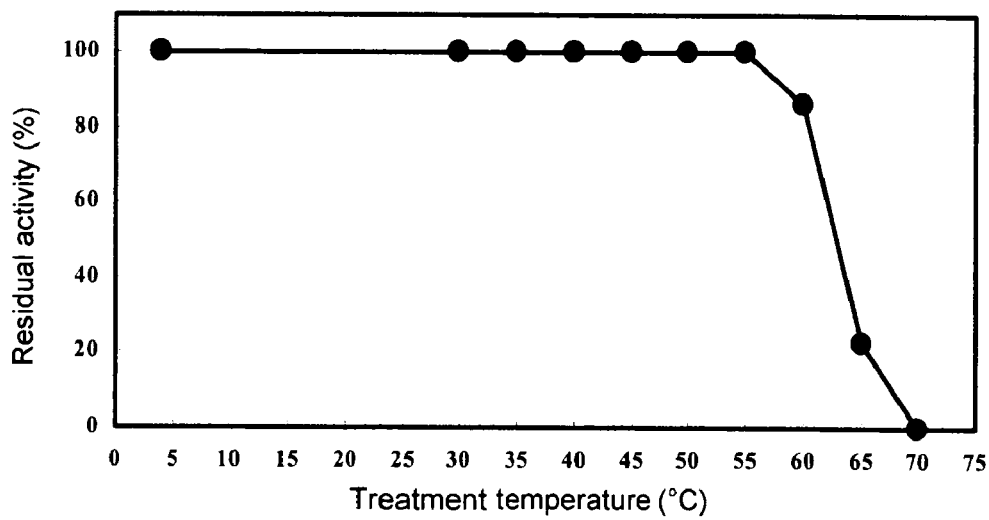
FIG. 14: Temperature/stability of the purified glyceroglycolipid lipase G-2 derived from strain SANK 11298 using lecithin as a substrate.

50 µl of a purified enzyme solution was added to 37.5 µl of 400 mM MOPS buffer (pH 6) and 62.5 µl of 1% TRITON X-100® solution which had been maintained at the treatment temperature. The mixture was stirred to homogeneity, incubated for 30 minutes, and then immediately cooled on ice. The glyceroglycolipid lipase G-2 as shown in Example 1. 3) was used as an enzyme. The measurement method was in accordance with the method as shown in Example 1. 2) 2. Relative residual degradation activities of the enzyme at respective temperatures are described below as relative values defining, as 100%, the residual activity under temperature conditions that resulted in the highest activity. The results are also shown in FIG. 14.

| Temperature/activity (FIGS. 14) | |
|---|---|
| Temperature (° C.) | Relative residual activity (%) |
| 4 | 100 |
| 30 | 100 |
| 35 | 100 |
| 40 | 100 |
| 45 | 100 |
| 50 | 100 |
| 55 | 100 |
| 60 | 86.2 |
| 65 | 22.5 |
| 70 | 0.0 |

In the present invention, the temperature at which a relative residual activity of 80% or more is retained is defined as the stable temperature. Thus, the stable temperature of the glyceroglycolipid lipase G-2 of the present invention using lecithin as a substrate is 4-60° C.

Test Example 2

Confirmation of Lysoglyceroglycolipid Generation

1) Sample Preparation

30 µl of 400 mM MOPS buffer (pH 6) and 30 µl of the glyceroglycolipid lipase enzyme G-2 as described in Example 1. 3) were added to 210 µl of the 2% DGDG solution as described in Example 1. 2) 1., and an enzymatic reaction was conducted at 37° C. for 4 hours. 1 µl of the mixture was spotted onto a 3×10 cm silica gel plate (No. 5626) using a capillary, and developed with a developing solvent. After the development, a coloring reagent was sprayed thereonto, and the plate was heated on a hot plate for color development.

TLC Conditions

Plate: Thin layer chromatography glass plate (Merck & Co., Inc., Silica Gel 60 No. 5626)

Developing solvent:chloroform:methanol:water:ethyl acetate:2-propanol (5:2:1:5:5)

Coloring reagent (orcinol-sulfuric acid): 20 mg of orcin monohydrate (Nacalai Tesque, Inc.) was dissolved in 1.1 ml of concentrated sulfuric acid, and the mixture was slowly added to 9 ml of distilled water stirred while cooling on ice to prepare a coloring reagent. (stored in a cool and dark place) Color development reaction: The coloring reagent was sprayed onto the plate after development, and the plate was heated on a hot plate for color development.
Rf values: DGDG: around 0.35; DGMG: around 0.20
2) Confirmation of DGMG by Mass Spectrum
The molecular weight was determined by the LC/MS method.
Measurement Conditions
LC: Waters Acquity
Column: HPLC BEH C18 2.1×100 mm 1.7 μm
Eluent conditions: A=$H_2O$ (0.1% HCOOH), B=$CH_3CN$
Gradient conditions: 0 min. 10% B 8 min. 100% B (2 min. Hold)
Flow rate: 0.2 ml/min.
MS: Waters LCT Premier XE
Ionizing method: ESI (+/−)
Cone voltage: +/−50V
DGDG or DGMG separated in 1) was separated by LC, and the molecular weight was determined for the maximum peak part using MS. Peaks were observed at m/z 974 for DGDG and at m/z 701 for DGMG.

Test Example 3

Baking test

1) Baking
280 g of strong flour, 11 g of butter, 2 tablespoonfuls of sugar, 1 tablespoonful of skim milk, 1 teaspoonful of salt, 200 ml of water, 1 teaspoonful of dry yeast, and 72.5 units (DGDG degradation activity) of the glyceroglycolipid lipase G-2 or the Lipopan F purified enzyme were mixed together, and the mixture was baked using a home bakery (Panasonic Corporation, SD-BT50). After baking, the bread was cooled to around room temperature, put in a vinyl bag. The bag was sealed, and then stored for one day in a thermostat bath at 20° C. in which a vat containing water was placed. Subsequently, specific volume bulk and the like were measured.
2) Specific Volume Bulk of Bread
Determination was carried out according to the rapeseed replacement method. When the glyceroglycolipid lipase G-2 of the present invention was added, 2.7% increase was observed as compared with that observed without the addition of the enzyme. Addition of the Lipopan F purified enzyme resulted in 13% decrease.
3) Flavor of Bread
1. Sensory Evaluation
The mean values for a cheese-like smell, which is unsuitable for bread, judged by three people one day after baking of bread are shown. The smell observed using the Lipopan F purified enzyme was defined as 10.

|  | No enzyme added | G-2 | Lipopan F purified enzyme |
|---|---|---|---|
| Cheese-like smell | 0 | 4 | 10 |

2. Analysis of Smell Components Using GC/MASS
About 1 g of the central part of the bread was analyzed under the following conditions:
GC/MS (EI) conditions
Apparatus (GC): HP6890 (Agilent)
(MS): MASS Sensitive Detector 5973N (Agilent)
Column: HP—INNOWAX (60 m·L*0.25·ID, 0.5 μm·Df) (Agilent)
Column flow rate: 1.8 ml/min. (constant flow)
Career gas: helium
Desorption conditions: 250° C. (for 8 minutes) at GC Injection
Inlet temperature: 250° C.
Column temperature: 40° C.: 13 min.–10° C./min.–250° C.*15 min.
Detector: MS (EI Scan-Positive)
Peaks were identified by comparison with the retention times for standards.
There were differences about the following compounds. Relative values are shown defining, as 100, the value observed using the Lipopan F purified enzyme.

|  | No enzyme added | G-2 | Lipopan F purified enzyme |
|---|---|---|---|
| Ethyl hexanoate | 22.5 | 26.4 | 100 |
| Ethyl octanoate | 15.9 | 46.3 | 100 |
| Ethyl decanoate | 12.1 | 65.7 | 100 |
| 9-Decenoic acid, ethyl ester | N.D. | 64.6 | 100 |
| Isopropyl myristate | N.D. | N.D. | 100 |
| Octanoic acid | N.D. | 43.2 | 100 |

Here, N.D. represents not detected. Among the above, it is generally known that octanoic acid gives a goat-cheese-like smell which is unsuitable for bread. The use of the enzyme of the present invention resulted in production of smaller quantities of the above compound.
As described above, the glyceroglycolipid lipase of the present invention is an enzyme that is derived from *Aspergillus japonicus* strain SANK 11298, is excellently safe, has the ability to hydrolyze neutral fat, glycerophospholipid, and glyceroglycolipid, has the highest activity at around weakly acidic pH, is thermostable to some extent, does not substantially hydrolyze lysoglyceroglycolipid or lysoglycerophospholipid, and has excellent effects in the fields of both the food industry and the baking industry.

The invention claimed is:

1. An isolated DNA selected from the group consisting of:
   a) a DNA consisting of the nucleotide sequence from nucleotide 110 to nucleotide 991 of SEQ ID NO: 1;
   b) a DNA comprising a nucleotide sequence at least 95% identical to SEQ ID NO:1 that encodes a protein having a glyceroglycolipid degradation activity;
   c) a DNA that remains hybridized to a nucleotide sequence consisting of nucleotides 110 to 991 of SEQ ID NO: 1 under stringent conditions which comprise washing hybridized DNA at 60° C. in 0.1×SSC, and wherein said DNA encodes a protein having a glyceroglycolipid degradation activity;
   d) a DNA encoding a protein comprising the amino acid sequence of SEQ ID NO: 2 or a protein comprising an amino acid sequence that is at least 95% identical to SEQ ID NO: 2, wherein the protein has glyceroglycolipid degradation activity; and
   e) a DNA comprising the nucleotide sequence of nucleotides 110 to 991 of SEQ ID NO: 1.

2. The isolated DNA of claim 1 that consists of the nucleotide sequence from nucleotide 110 to nucleotide 991 of SEQ ID NO: 1.

3. The isolated DNA of claim 1 that comprises a nucleotide sequence at least 95% identical to the nucleotide sequence of nucleotides 110 to 991 of SEQ ID NO: 1 and that encodes a protein having a glyceroglycolipid degradation activity.

4. The isolated DNA of claim 1, wherein the DNA remains hybridized to a DNA consisting of the nucleotide sequence of nucleotides 110 to 991 of SEQ ID NO: 1 under stringent conditions that comprise washing hybridized DNA at 60° C. in 0.1×SSC, and that encodes a protein having a glyceroglycolipid degradation activity.

5. The isolated DNA of claim 1 that encodes a protein comprising the amino acid sequence of SEQ ID NO: 2 or a protein comprising an amino acid sequence that is at least 95% identical to SEQ ID NO: 2, wherein the protein has glyceroglycolipid degradation activity.

6. The isolated DNA of claim 1 that comprises the nucleotide sequence from nucleotides 110 to 991 of SEQ ID NO: 1.

7. A vector comprising the isolated DNA of claim 1.

8. The vector of claim 7 that is a vector for a prokaryotic cell.

9. The vector of claim 7 that is a vector for a eukaryotic cell.

10. A host cell transformed with the vector of claim 7.

11. A prokaryotic cell transformed with the vector of claim 8.

12. A eukaryotic cell transformed with the vector of claim 9.

13. A method for making a glyceroglycolipase encoded by the isolated DNA of claim 1, comprising expressing a host cell containing said isolated DNA under conditions suitable for expression of said glyceroglycolipase.

14. The method of claim 13, wherein the host cell is a prokaryote.

15. The method of claim 13, wherein the host cell is a eukaryote.

\* \* \* \* \*